(12) United States Patent
Morita

(10) Patent No.: US 12,327,352 B2
(45) Date of Patent: *Jun. 10, 2025

(54) IMAGE SETTING DEVICE, IMAGE SETTING METHOD, AND IMAGE SETTING PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 454 days.

This patent is subject to a terminal disclaimer.

(21) Appl. No.: 17/811,883

(22) Filed: Jul. 12, 2022

(65) Prior Publication Data

US 2022/0358649 A1 Nov. 10, 2022

Related U.S. Application Data

(63) Continuation of application No. PCT/JP2020/045511, filed on Dec. 7, 2020.

(30) Foreign Application Priority Data

Feb. 4, 2020 (JP) .................................. 2020-017414

(51) Int. Cl.
G06T 7/00 (2017.01)
(52) U.S. Cl.
CPC .. *G06T 7/0012* (2013.01); *G06T 2207/30068* (2013.01)
(58) Field of Classification Search
CPC ......... G06T 7/0012; G06T 2207/30068; A61B 6/025; A61B 6/5223; A61B 6/5241; G16H 30/20; G16H 30/40; G16H 50/50
See application file for complete search history.

(56) References Cited

U.S. PATENT DOCUMENTS 8,983,156 B2 3/2015 Periaswamy et al.
9,792,703 B2 10/2017 Costa et al.
(Continued)

FOREIGN PATENT DOCUMENTS

EP 3011905 A1 4/2016
EP 2814396 B1 6/2017
(Continued)

OTHER PUBLICATIONS

English language translation of the following: Decision of Refusal dated Feb. 7, 2023 from the JPO in a Japanese patent application No. 2021-575631 corresponding to the instant patent application. This office action translation is submitted now in order to supplement the understanding of the cited references which are being disclosed in the instant Information Disclosure Statement.

(Continued)

*Primary Examiner* — Carol W Chan
(74) *Attorney, Agent, or Firm* — SOLARIS Intellectual Property Group, PLLC

(57) ABSTRACT

A processor is configured to generate a structure-highlighted synthesized two-dimensional image from a plurality of tomographic images, to detect a structure of interest from the plurality of tomographic images or the structure-highlighted synthesized two-dimensional image, and to set at least some of the plurality of tomographic images as either storage-required images or non-storage-required images based on a detection result of the structure of interest.

26 Claims, 29 Drawing Sheets

(56) References Cited

U.S. PATENT DOCUMENTS

| | | |
|---|---|---|
| 2004/0101095 A1 | 5/2004 | Jing et al. |
| 2005/0113681 A1 | 5/2005 | DeFreitas et al. |
| 2006/0098855 A1 | 5/2006 | Gkanatsios et al. |
| 2006/0173303 A1 | 8/2006 | Yu et al. |
| 2006/0228012 A1* | 10/2006 | Masuzawa ............ G06T 11/008 382/131 |
| 2007/0030949 A1 | 2/2007 | Jing et al. |
| 2008/0019581 A1 | 1/2008 | Gkanatsios et al. |
| 2008/0075341 A1 | 3/2008 | Goto |
| 2008/0130979 A1 | 6/2008 | Ren et al. |
| 2009/0003519 A1 | 1/2009 | Defreitas et al. |
| 2009/0010384 A1 | 1/2009 | Jing et al. |
| 2009/0123052 A1 | 5/2009 | Ruth et al. |
| 2009/0141859 A1 | 6/2009 | Gkanatsios et al. |
| 2009/0213987 A1 | 8/2009 | Stein et al. |
| 2009/0268865 A1 | 10/2009 | Ren et al. |
| 2009/0296882 A1 | 12/2009 | Gkanatsios et al. |
| 2010/0135456 A1 | 6/2010 | Jing et al. |
| 2010/0135558 A1 | 6/2010 | Ruth et al. |
| 2010/0195882 A1 | 8/2010 | Ren et al. |
| 2011/0069808 A1 | 3/2011 | Defreitas et al. |
| 2011/0069809 A1 | 3/2011 | Defreitas et al. |
| 2011/0135185 A1 | 6/2011 | Gkanatsios et al. |
| 2011/0157154 A1 | 6/2011 | Bernard et al. |
| 2011/0216879 A1 | 9/2011 | Jing et al. |
| 2012/0195484 A1 | 8/2012 | Ren et al. |
| 2012/0219111 A1 | 8/2012 | Defreitas et al. |
| 2013/0028374 A1 | 1/2013 | Gkanatsios et al. |
| 2013/0223591 A1 | 8/2013 | Jing et al. |
| 2013/0272494 A1 | 10/2013 | Defreitas et al. |
| 2014/0033126 A1 | 1/2014 | Kreeger et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0147025 A1 | 5/2014 | Periaswamy et al. |
| 2014/0232752 A1 | 8/2014 | Ren et al. |
| 2014/0301529 A1 | 10/2014 | Ren et al. |
| 2014/0327702 A1 | 11/2014 | Kreeger et al. |
| 2014/0376690 A1 | 12/2014 | Jing et al. |
| 2015/0049859 A1 | 2/2015 | Defreitas et al. |
| 2015/0160848 A1 | 6/2015 | Gkanatsios et al. |
| 2015/0182181 A1 | 7/2015 | Ruth et al. |
| 2015/0310611 A1 | 10/2015 | Gkanatsios et al. |
| 2015/0317538 A1 | 11/2015 | Ren et al. |
| 2015/0356757 A1 | 12/2015 | Marshall |
| 2016/0206273 A1 | 7/2016 | Fukuda |
| 2016/0220210 A1 | 8/2016 | Ruth et al. |
| 2016/0367210 A1 | 12/2016 | Gkanatsios et al. |
| 2017/0011534 A1 | 1/2017 | Costa et al. |
| 2017/0024113 A1 | 1/2017 | Gkanatsios et al. |
| 2017/0128028 A1 | 5/2017 | Defreitas et al. |
| 2017/0135650 A1 | 5/2017 | Stein et al. |
| 2018/0055470 A1 | 3/2018 | Ruth et al. |
| 2018/0137385 A1 | 5/2018 | Ren et al. |
| 2018/0177476 A1 | 6/2018 | Jing et al. |
| 2018/0188937 A1 | 7/2018 | Gkanatsios et al. |
| 2018/0289347 A1 | 10/2018 | Defreitas et al. |
| 2018/0344276 A1 | 12/2018 | Defreitas et al. |
| 2019/0043456 A1 | 2/2019 | Kreeger et al. |
| 2019/0053776 A1 | 2/2019 | Ruth et al. |
| 2019/0095087 A1 | 3/2019 | Gkanatsios |
| 2019/0125286 A1 | 5/2019 | Gkanatsios et al. |
| 2019/0200942 A1 | 7/2019 | Defreitas et al. |
| 2019/0325255 A1 | 10/2019 | Ren et al. |
| 2020/0012417 A1 | 1/2020 | Gkanatsios et al. |
| 2020/0022663 A1 | 1/2020 | Ren et al. |
| 2020/0253573 A1 | 8/2020 | Gkanatsios et al. |
| 2020/0258479 A1 | 8/2020 | Kreeger et al. |
| 2020/0348835 A1 | 11/2020 | Gkanatsios et al. |
| 2021/0049731 A1* | 2/2021 | Fukuda ................. G06T 1/0007 |
| 2021/0059622 A1* | 3/2021 | Fukuda .................. A61B 6/463 |
| 2021/0128087 A1 | 5/2021 | Defreitas et al. |
| 2021/0204894 A1 | 7/2021 | Ren et al. |
| 2021/0233239 A1* | 7/2021 | Li .......................... G16H 30/40 |
| 2022/0013089 A1 | 1/2022 | Kreeger et al. |
| 2022/0071582 A1 | 3/2022 | Defreitas et al. |

FOREIGN PATENT DOCUMENTS

| | | |
|---|---|---|
| JP | 2008-83830 A | 4/2008 |
| JP | 2014-128716 A | 7/2014 |
| JP | 2015-535466 A | 12/2015 |
| JP | 2016-502917 A | 2/2016 |
| JP | 2016-131573 A | 7/2016 |
| JP | 2017-510323 A | 4/2017 |

OTHER PUBLICATIONS

International Search Report issued in International Application No. PCT/JP2020/045511 on Feb. 22, 2021.

Written Opinion of the ISA issued in International Application No. PCT/JP2020/045511 on Feb. 22, 2021.

Extended European Search Report dated Jun. 12, 2023, issued in corresponding EP Patent Application No. 20917436.6.

* cited by examiner

IMAGE SETTING DEVICE, IMAGE SETTING METHOD, AND IMAGE SETTING PROGRAM

CROSS REFERENCE TO RELATED APPLICATIONS

The present application is a Continuation of PCT International Application No. PCT/JP2020/045511, filed on Dec. 7, 2020, which claims priority to Japanese Patent Application No. 2020-017414, filed on Feb. 4, 2020. Each application above is hereby expressly incorporated by reference, in its entirety, into the present application.

BACKGROUND

Technical Field

The present disclosure relates to an image setting device, an image setting method, and an image setting program.

Related Art

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image, and imaging is performed on the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art which irradiates an object with radiation in a predetermined direction.

In addition, a technique has been known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method to generate a pseudo two-dimensional image (hereinafter, referred to as a synthesized two-dimensional image) corresponding to the simple two-dimensional image (see JP2014-128716A). In the synthesized two-dimensional image, an abnormal part included in the tomographic image is less affected by the tissues in the thickness direction of the breast than that in the simple two-dimensional image. Therefore, the use of the synthesized two-dimensional image makes it easy to interpret an abnormal part in the breast with one image.

In contrast, in the medical field, a computer aided diagnosis (hereinafter, referred to as CAD) system has been known which automatically detects a structure, such as an abnormal shadow, in an image and displays the detected structure so as to be highlighted. For example, the CAD is used to detect important diagnostic structure, such as a calcification, a spicula, and a tumor, from the tomographic images acquired by the tomosynthesis imaging. In addition, a method has been proposed which, in a case in which a synthesized two-dimensional image is generated from a plurality of tomographic images acquired by performing the tomosynthesis imaging on the breast, detects a region of interest including a structure using the CAD and combines the detected region of interest on, for example, a projection image or a two-dimensional image acquired by simple imaging to generate a synthesized two-dimensional image (see the specification of U.S. Pat. No. 8,983,156B). Further, a method has been proposed which combines tomographic images including only the structure detected by the CAD to generate a synthesized two-dimensional image (see the specification of U.S. Pat. No. 9,792,703B). The use of the methods disclosed in the specification of U.S. Pat. No. 8,983,156B or the specification of U.S. Pat. No. 9,792,703B makes it possible to generate a synthesized two-dimensional image in which an abnormal shadow is easily observed since the structure, such as the abnormal shadow, is highlighted.

Further, in some cases, comparative observation over time is performed using the past radiographic images in order to diagnose the healing state or the progress state of a disease. In this case, radiographic images acquired by the latest examination and radiographic images acquired by the past examination are transmitted from a picture archiving and communication system (PACS) that stores a plurality of images for diagnosis to an image interpretation terminal, and a radiologist performs comparative image interpretation.

However, the tomosynthesis imaging is performed to acquire a plurality of tomographic images. However, as the number of images used for diagnosis increases, the storage capacity of the images in the PACS increases. Therefore, a storage cost increases. In addition, it takes time to transmit an image from a console of an imaging apparatus to the PACS and further from the PACS to an image interpretation terminal, which results in an increase in the transmission cost. Therefore, a method has been proposed which combines every predetermined number of tomographic images among a plurality of tomographic images to generate slab images and stores or transmits the slab images (see JP2017-510323A). According to the method disclosed in JP2017-510323A, it is possible to reduce the number of tomographic images. Therefore, it is possible to reduce a cost for storing or transmitting the images.

However, even in a case in which the slab image is generated as in the method disclosed in JP2017-510323A, the amount of data of the images to be stored or transmitted is still large. Therefore, it is desired to further reduce the cost for storage or transmission.

SUMMARY OF THE INVENTION

The present disclosure has been made in view of the above circumstances, and an object of the present disclosure is to further reduce a cost for storing or transmitting an image acquired by tomosynthesis imaging.

According to the present disclosure, there is provided an image setting device comprising at least one processor. The processor is configured to generate a structure-highlighted synthesized two-dimensional image from a plurality of tomographic images, to detect a structure of interest from the plurality of tomographic images or the structure-highlighted synthesized two-dimensional image, and to set at least some of the plurality of tomographic images as either storage-required images or non-storage-required images based on a detection result of the structure of interest.

The "structure-highlighted synthesized two-dimensional image" is a pseudo two-dimensional image generated by combining a plurality of tomographic images and is a synthesized two-dimensional image in which a structure, such as an abnormal shadow, included in the tomographic image has been highlighted by the method disclosed, for example, in the specification of U.S. Pat. No. 8,983,156B and the specification of the specification of U.S. Pat. No. 9,792,703B.

The "storage-required image" means an image that needs to be stored or transmitted to an external device. The "non-storage-required image" means an image that does not need to be stored or transmitted to the external device.

Further, in the image setting device according to the present disclosure, the processor may be configured to set at least some of the plurality of tomographic images and the structure-highlighted synthesized two-dimensional image as the storage-required images in a case in which the structure of interest is detected.

Furthermore, in the image setting device according to the present disclosure, the processor may be configured to set at least some of the plurality of tomographic images as the non-storage-required images and to set the structure-highlighted synthesized two-dimensional image as the storage-required image in a case in which the structure of interest is not detected.

Moreover, in the image setting device according to the present disclosure, the processor may be configured to set at least some of the plurality of tomographic images as the non-storage-required images and to set the structure-highlighted synthesized two-dimensional image as the storage-required image in a case in which the structure of interest is detected.

In addition, in the image setting device according to the present disclosure, the processor may be configured to set at least some of the plurality of tomographic images and the structure-highlighted synthesized two-dimensional image as the storage-required images in a case in which the structure of interest is not detected.

Further, in the image setting device according to the present disclosure, the processor may be configured to receive a setting of determining at least some of the plurality of tomographic images as the storage-required images or the non-storage-required images in a case in which the structure of interest is not detected and to set at least some of the plurality of tomographic images and the structure-highlighted synthesized two-dimensional image as the storage-required images in a case in which the structure of interest is not detected and the setting of determining at least some of the plurality of tomographic images as the storage-required image is received.

Further, in the image setting device according to the present disclosure, the processor may be configured to receive a setting of determining at least some of the plurality of tomographic images as the storage-required images or the non-storage-required images in a case in which the structure of interest is not detected and to set at least some of the plurality of tomographic images as the non-storage-required images and set the structure-highlighted synthesized two-dimensional image as the storage-required image in a case in which the structure of interest is not detected and the setting of determining at least some of the plurality of tomographic images as the non-storage-required image is received.

Moreover, in the image setting device according to the present disclosure, the processor may be configured to set at least some of the plurality of tomographic images as the non-storage-required images and to set the structure-highlighted synthesized two-dimensional image as the storage-required image in a case in which the structure of interest is detected.

Further, in the image setting device according to the present disclosure, the processor may be configured to set at least some of the plurality of tomographic images and the structure-highlighted synthesized two-dimensional image as the storage-required images in a case in which the structure of interest is detected.

Furthermore, in the image setting device according to the present disclosure, the processor may be configured to receive a setting of determining at least some of the plurality of tomographic images as the storage-required images or the non-storage-required images in a case in which the structure of interest is detected and to set at least some of the plurality of tomographic images and the structure-highlighted synthesized two-dimensional image as the storage-required images in a case in which the structure of interest is detected and the setting of determining at least some of the plurality of tomographic images as the storage-required image is received.

Furthermore, in the image setting device according to the present disclosure, the processor may be configured to receive a setting of determining at least some of the plurality of tomographic images as the storage-required images or the non-storage-required images in a case in which the structure of interest is detected and to set at least some of the plurality of tomographic images as the non-storage-required images and set the structure-highlighted synthesized two-dimensional image as the storage-required image in a case in which the structure of interest is detected and the setting of determining at least some of the plurality of tomographic images as the non-storage-required image is received.

Furthermore, in the image setting device according to the present disclosure, the processor may be configured to set at least some of the plurality of tomographic images as the non-storage-required images and to set the structure-highlighted synthesized two-dimensional image as the storage-required image in a case in which the structure of interest is not detected.

In addition, in the image setting device according to the present disclosure, the processor may be configured to set at least some of the plurality of tomographic images and the structure-highlighted synthesized two-dimensional image as the storage-required images in a case in which the structure of interest is not detected.

Further, in the image setting device according to the present disclosure, the processor may be configured to set whether or not to generate the structure-highlighted synthesized two-dimensional image from the plurality of tomographic images and to generate the structure-highlighted synthesized two-dimensional image in a case in which the structure-highlighted synthesized two-dimensional image is set to be generated.

Furthermore, in the image setting device according to the present disclosure, the processor may be configured to set at least some of the plurality of tomographic images as the storage-required images in a case in which the structure-highlighted synthesized two-dimensional image is set not to be generated.

Further, in the image setting device according to the present disclosure, the processor may be configured to receive a setting of determining at least some of the plurality of tomographic images as the storage-required images or the non-storage-required images in a case in which the structure-highlighted synthesized two-dimensional image is set not to be generated and to set at least some of the plurality of tomographic images as the storage-required images in a case in which the setting of determining at least some of the plurality of tomographic images as the storage-required images is received.

Furthermore, in the image setting device according to the present disclosure, in a case in which the structure-highlighted synthesized two-dimensional image is set not to be generated, the processor may be configured to generate another synthesized two-dimensional image different from the structure-highlighted synthesized two-dimensional image from the plurality of tomographic images and to set another synthesized two-dimensional image as the storage-required image.

The "another synthesized two-dimensional image different from the structure-highlighted synthesized two-dimensional image" is, for example, a pseudo two-dimensional image that is generated by the method disclosed in JP2014-128716A and is generated by combining a plurality of tomographic images having different distances (positions in a height direction) from a detection surface of a radiation detector to a radiation source using an addition method, an averaging method, a maximum intensity projection method, a minimum intensity projection method, or the like and is a synthesized two-dimensional image in which a structure is not highlighted and which is different from the synthesized two-dimensional image generated by the method disclosed in the specification of U.S. Pat. No. 8,983,156B or the specification of U.S. Pat. No. 9,792,703B.

Further, in the image setting device according to the present disclosure, the processor may be configured to store an image set as the storage-required image in a storage.

In this case, the processor may be configured to store information indicating a detection result of the structure of interest in the storage.

Further, in the image setting device according to the present disclosure, the processor may be configured to transmit an image set as the storage-required image to an external device.

In this case, the processor may be configured to transmit information indicating a detection result of the structure of interest to the external device.

Furthermore, in the image setting device according to the present disclosure, at least some of the plurality of tomographic images may be tomographic images in which the structure of interest has been detected.

Moreover, in the image setting device according to the present disclosure, at least some of the plurality of tomographic images may be a plurality of slab images obtained by increasing a thickness of each of the plurality of tomographic images.

The "increasing the thickness of each of the plurality of tomographic images" means combining some tomographic images included in the plurality of tomographic images using addition, weighting and addition, or the like to generate one tomographic image from some of the plurality of tomographic images. Therefore, one tomographic image generated from a plurality of tomographic images is a slab image.

In addition, in the image setting device according to the present disclosure, the processor may be configured to reconstruct a plurality of projection images acquired by performing tomosynthesis imaging on an object to acquire the plurality of tomographic images.

Further, in the image setting device according to the present disclosure, an object included in the plurality of tomographic images may be a breast, and the structure of interest may include at least one candidate of a calcification, a tumor, or a spicula.

According to the present disclosure, there is provided an image setting method comprising: generating a structure-highlighted synthesized two-dimensional image from a plurality of tomographic images; detecting a structure of interest from the plurality of tomographic images or the structure-highlighted synthesized two-dimensional image; and setting at least some of the plurality of tomographic images as either storage-required images or non-storage-required images based on a detection result of the structure of interest.

In addition, a program that causes a computer to perform the image setting method according to the present disclosure may be provided.

According to the present disclosure, it is possible to further reduce a cost for storage or transmission.

DETAILED DESCRIPTION

Figure 1:
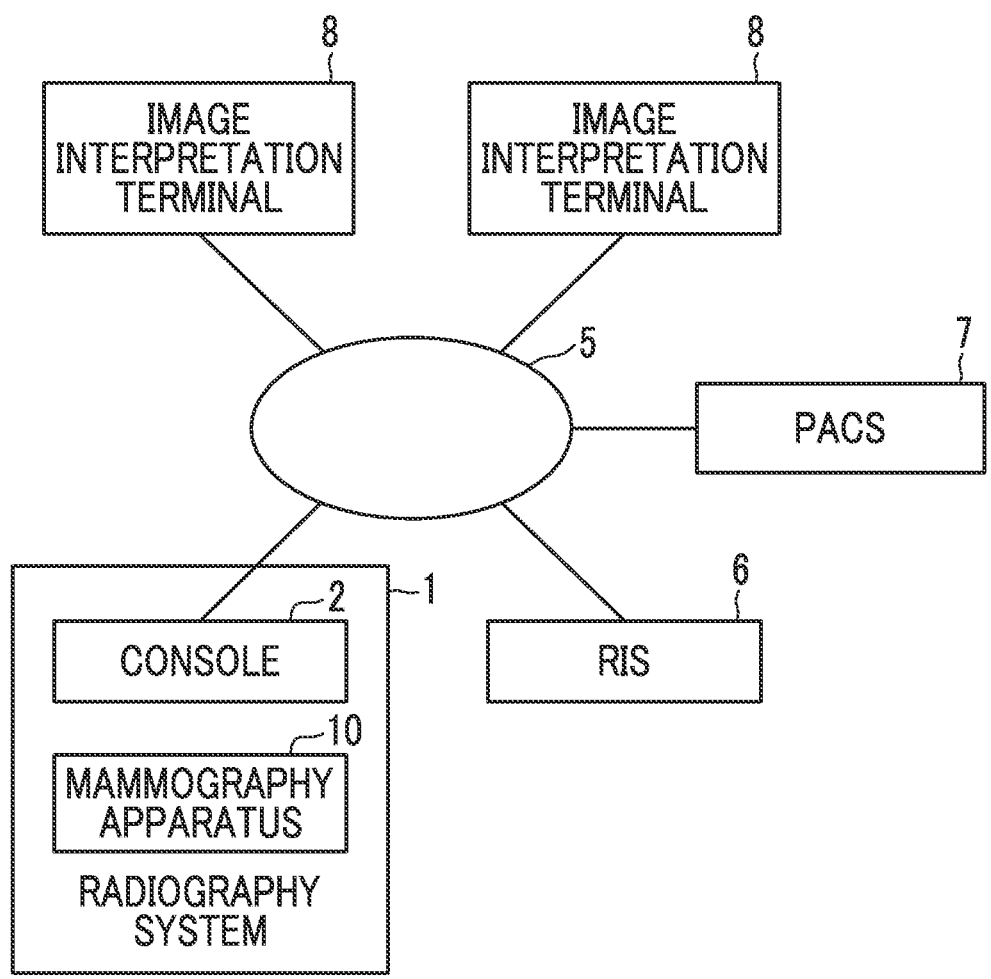
FIG. 1 is a diagram schematically illustrating a configuration of a radiographic image interpretation system to which an image setting device according to a first embodiment of the present disclosure is applied.

Hereinafter, embodiments of the present disclosure will be described with reference to the drawings. FIG. 1 is a diagram schematically illustrating a configuration of a radiographic image interpretation system to which an image setting device according to an embodiment of the present disclosure is applied. As illustrated in FIG. 1, in the radiographic image interpretation system according to this embodiment, a radiography system 1 including a console 2 and a mammography apparatus 10, a radiology information system (RIS) 6, a picture archiving and communication system (PACS) 7, and a plurality of image interpretation terminals (two image interpretation terminals in FIG. 1) 8 are connected through a network 5 so as to communicate with each other.

Figure 2:
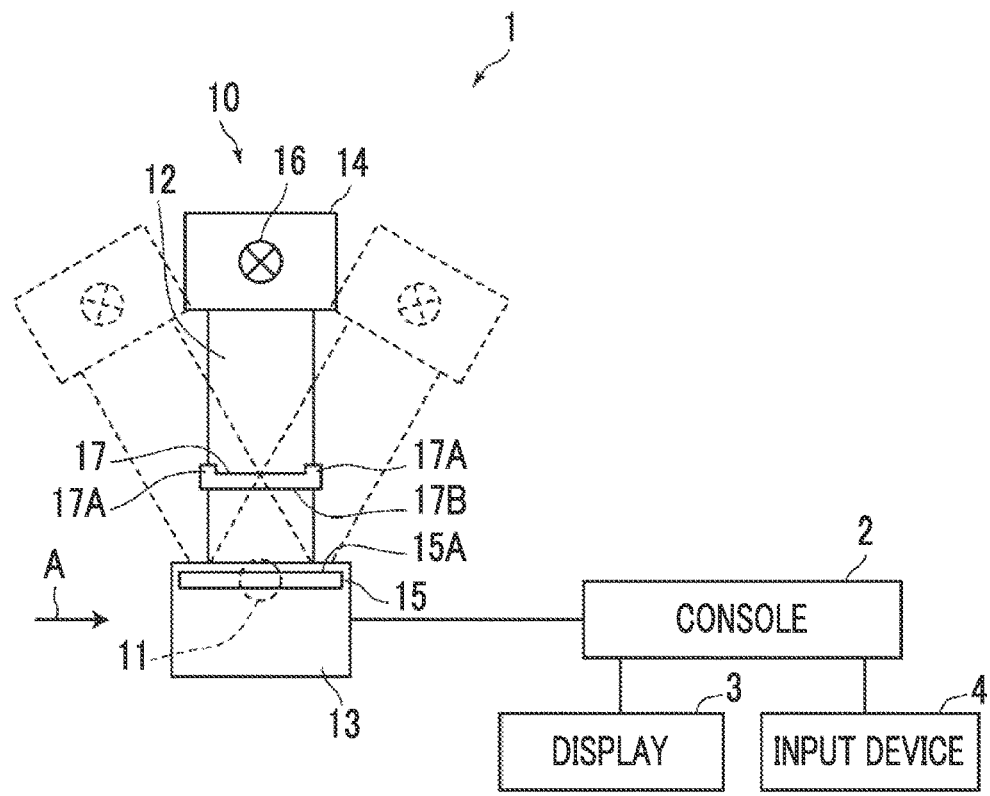
FIG. 2 is a diagram schematically illustrating the configuration of the radiography system.
Figure 3:
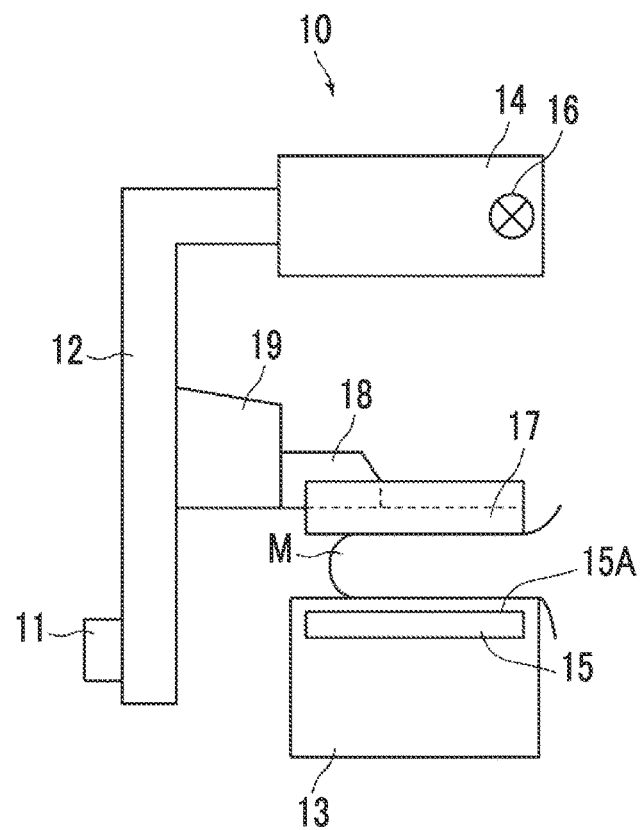
FIG. 3 is a diagram illustrating a mammography apparatus as viewed from a direction of an arrow A in FIG. 2.

FIG. 2 is a diagram schematically illustrating a configuration of the radiography system and FIG. 3 is a diagram illustrating the mammography apparatus included in the radiography system as viewed from the direction of an arrow A in FIG. 2.

As illustrated in FIG. 2, the radiography system 1 includes the console 2 and the mammography apparatus 10. The console 2 comprises a display 3 and an input device 4. The console 2 is connected to the RIS 6 and the PACS 7 through the network 5 such that it can communicate therewith.

The radiography system 1 according to this embodiment has a function of capturing the images of a breast M using the mammography apparatus 10 on the basis of an instruction (imaging order) input from the RIS 6 through the console 2 in response to an operation of an operator, such as a doctor or a radiology technician, and acquiring a tomographic image and a synthesized two-dimensional image of the breast M. In this embodiment, the mammography apparatus 10 can perform both tomosynthesis imaging and simple imaging in various imaging directions to generate a tomographic image and a two-dimensional breast image of the breast M. The two-dimensional breast image means a breast image acquired by the simple imaging. An image set including the tomographic image and the synthesized two-dimensional image generated in the radiography system 1 as described below is transmitted to the PACS 7 and is then stored therein. Further, the image set may be stored in the radiography system 1.

The mammography apparatus 10 comprises an arm portion 12 that is connected to a base (not illustrated) by a rotation shaft 11. An imaging table 13 is attached to one end of the arm portion 12, and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed and only the radiation emitting unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

The radiation detector 15 can repeatedly perform the recording and reading of a radiographic image and may be a so-called direct-type radiation detector that directly converts radiation into charge or a so-called indirect-type radiation detector that converts radiation into visible light once and converts the visible light into a charge signal. As a method for reading a radiographic image signal, it is desirable to use the following method: a so-called thin film transistor (TFT) reading method which turns on and off a TFT switch to read a radiographic image signal; or a so-called optical reading method which emits reading light to read a radiographic image signal. However, the reading method is not limited thereto and other methods may be used.

A radiation source 16 is accommodated in the radiation emitting unit 14. The radiation source 16 emits, for example, X-rays as radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that presses and compresses the breast M, a support portion 18 that supports the compression plate 17, and a movement mechanism 19 that moves the support portion 18 in the vertical direction in FIGS. 2 and 3. An interval between the compression plate 17 and the imaging table 13, that is, a compression thickness is input to the console 2. In addition, the compression plates 17 having a plurality of sizes and shapes corresponding to the types of imaging are prepared. Therefore, the compression plate 17 is attached to the support portion 18 so as to be interchangeable. Further, side walls 17A are formed on the left and right edges of the compression plate 17 in FIG. 2. The side walls 17A are formed in order to reduce the pain of a patient in a case in which the breast M compressed by a compression surface 17B of the compression plate 17 protrudes from the compression plate 17.

The display 3 is a display device, such as a cathode ray tube (CRT) or a liquid crystal display, and displays messages required for operations in addition to a tomographic image and a synthesized two-dimensional image which will be described below. In addition, the display 3 may include a speaker that outputs sound.

The input device 4 consists of a keyboard, a mouse, or a touch-panel-type input device and receives an instruction to operate the mammography apparatus 10 from the operator. In addition, the input device 4 receives the input of various kinds of information required for tomosynthesis imaging, such as imaging conditions, and an instruction to correct information. In this embodiment, each unit of the mammography apparatus 10 is operated according to the information input by the operator through the input device 4.

An imaging program for performing, for example, tomosynthesis imaging and an image setting program according to this embodiment are installed in the console 2. The console 2 corresponds to the image setting device according to this embodiment. In this embodiment, the console 2 may be a workstation or a personal computer that is directly operated by the operator or a server computer that is connected to them through a network. The imaging program is stored in a storage device of a server computer connected to the network or a network storage in a state in which it can be accessed from the outside and is downloaded and installed in the computer as required. Alternatively, the imaging control program is recorded on a recording medium, such as a digital versatile disc (DVD) or a compact disc read only memory (CD-ROM), is distributed, and is installed in a computer from the recording medium.

Figure 4:
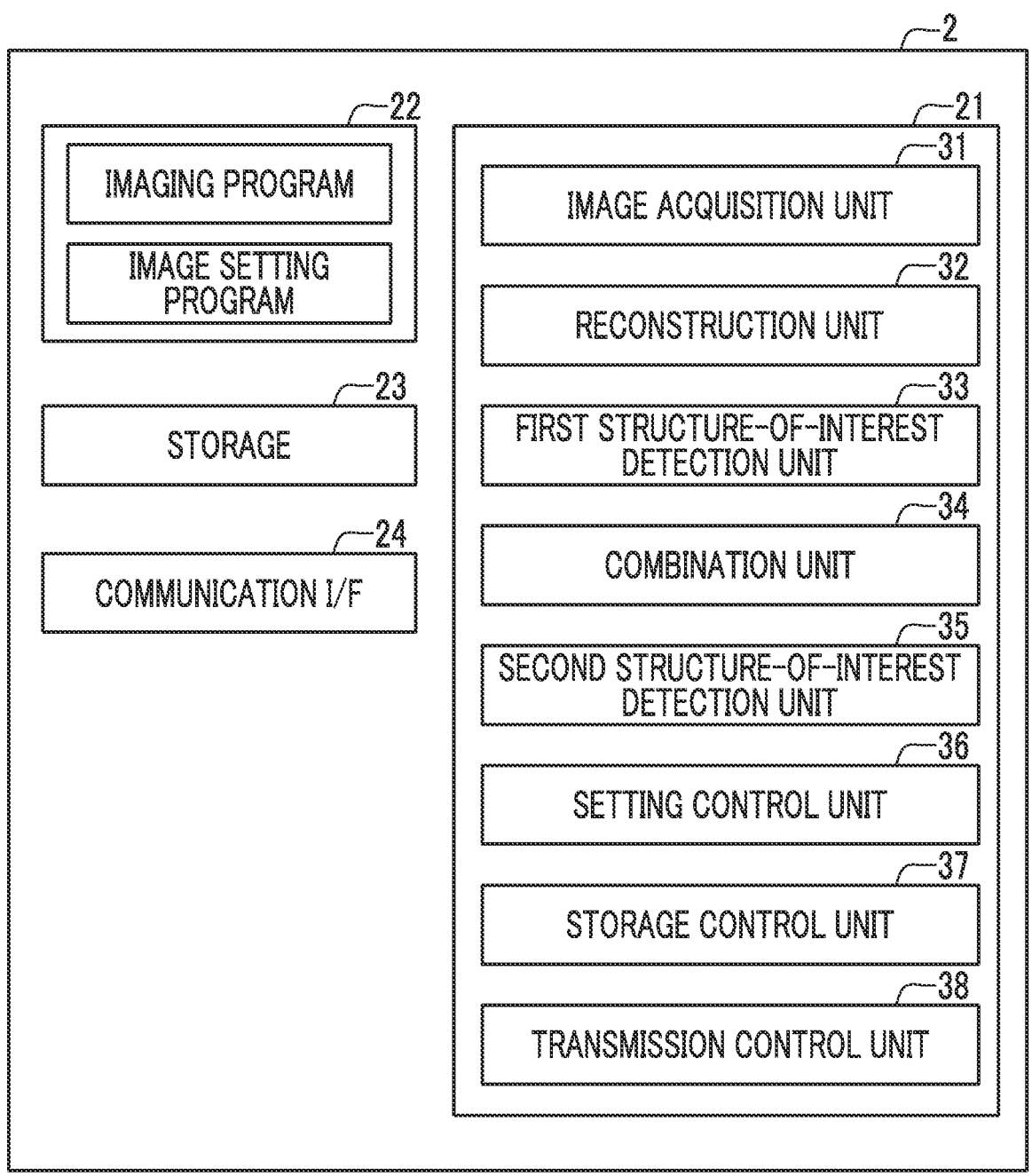
FIG. 4 is a diagram schematically illustrating a configuration of the image setting device according to the first embodiment of the present disclosure that is implemented by installing an imaging program and an image setting program in a computer constituting a console.

FIG. 4 is a diagram schematically illustrating the configuration of the image setting device that is implemented by installing the imaging program and the image setting program in a computer constituting the console 2. As illustrated in FIG. 4, the image setting device comprises a central processing unit (CPU) 21, a memory 22, a storage 23, and a communication interface (I/F) 24 as a standard computer configuration.

The storage 23 consists of a storage device, such as a hard disk drive or a solid state drive (SSD), and stores various kinds of information including the imaging program and the image setting program for driving each unit of the mammography apparatus 10 to perform the tomosynthesis imaging. Further, for example, projection images acquired by imaging, and a plurality of tomographic images and synthesized two-dimensional images generated as described below are stored in the storage 23.

The communication I/F 24 is a network interface that controls the transmission of various kinds of information through the network 5.

The memory 22 temporarily stores, for example, the imaging program and the image setting program stored in the storage 23 in order to cause the CPU 21 to perform various processes. The imaging program defines, as a process to be executed by the CPU 21, an image acquisition process that causes the mammography apparatus 10 to perform tomosynthesis imaging to acquire a plurality of projection images of the breast M corresponding to each of a plurality of radiation source positions. The image setting program defines the following processes as the processes to be executed by the CPU 21: a reconstruction process that reconstructs the plurality of projection images to generate a plurality of tomographic images in each of a plurality of tomographic planes of the breast M which is an object; a first structure-of-interest detection process that detects, as structures of interest, important diagnostic structures, such as a calcification, a spicula, and a tumor, from the plurality of tomographic images; a combination process that generates a structure-highlighted synthesized two-dimensional image from the plurality of tomographic images; a second structure-of-interest detection process that detects, as the structures of interest, important diagnostic structures, such as a calcification, a spicula, and a tumor, from the plurality of tomographic images or the structure-highlighted synthesized two-dimensional image; a setting control process that sets at least some of the plurality of tomographic images as storage-required images or non-storage-required images according to a detection result of the structure of interest; a storage control process that stores the image set as the storage-required image in the storage 23; and a transmission control process that transmits the image set as the storage-required image to the PACS 7.

Then, the CPU 21 performs a process according to the imaging program such that the CPU 21 functions as an image acquisition unit 31. Further, the CPU 21 performs a process according to the image setting program to function as a reconstruction unit 32, a first structure-of-interest detection unit 33, a combination unit 34, a second structure-ofinterest detection unit 35, a setting control unit 36, a storage control unit 37, and a transmission control unit 38.

Figure 5:
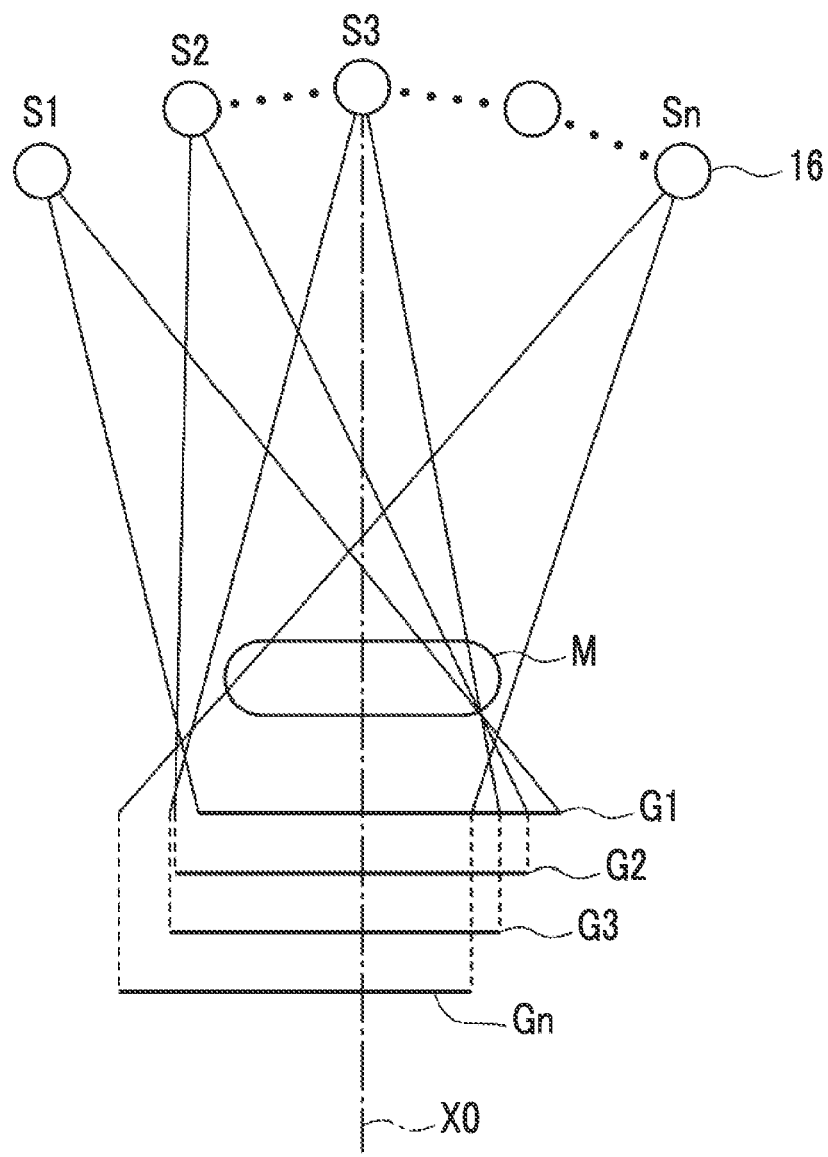
FIG. 5 is a diagram illustrating the acquisition of projection images.

The image acquisition unit 31 rotates the arm portion 12 around the rotation shaft 11 to move the radiation source 16, irradiates the breast M with radiation at a plurality of radiation source positions caused by the movement of the radiation source 16 according to imaging conditions for tomosynthesis imaging, detects the radiation transmitted through the breast M using the radiation detector 15, and acquires a plurality of projection images Gi (i=1 to n, where n is the number of radiation source positions and is, for example, 15) at the plurality of radiation source positions. FIG. 5 is a diagram illustrating the acquisition of the projection images Gi. As illustrated in FIG. 5, the radiation source 16 is moved to each of radiation source positions S1, S2, . . . , Sc, . . . , and Sn. The radiation source 16 is driven at each radiation source position to irradiate the breast M with radiation. The radiation detector 15 detects the radiation transmitted through the breast M to acquire projection images G1, G2, . . . , Gc, . . . , and Gn corresponding to the radiation source positions S1 to Sn, respectively. Here, the radiation source position Sc illustrated in FIG. 5 is a radiation source position where an optical axis X0 of the radiation emitted from the radiation source 16 is orthogonal to the detection surface 15A of the radiation detector 15. Hereinafter, it is assumed that the radiation source position Sc is referred to as a reference radiation source position Sc. At each of the radiation source positions S1 to Sn, the same dose of radiation is emitted to the breast M. The plurality of acquired projection images Gi are stored in the storage 23.

Figure 6:
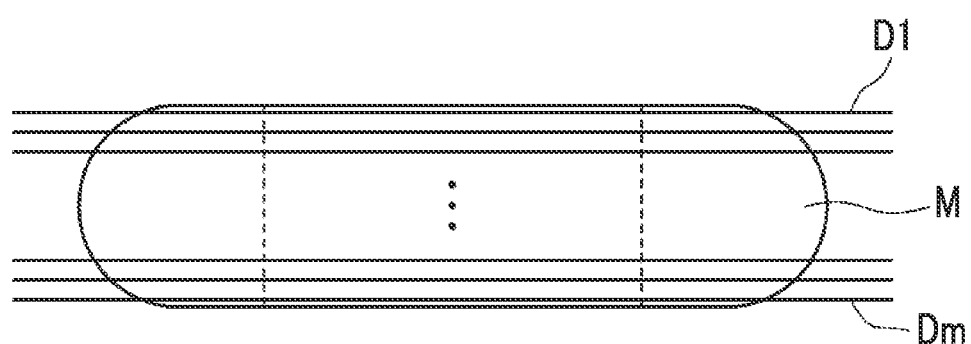
FIG. 6 is a diagram illustrating the generation of tomographic images.

The reconstruction unit 32 reconstructs the projection images Gi to generate the tomographic images in which the desired tomographic planes of the breast M have been highlighted. Specifically, the reconstruction unit 32 reconstructs the plurality of projection images Gi using a known back projection method, such as a simple back projection method or a filtered back projection method, to generate a plurality of tomographic images Dj (j=1 to m) in each of the plurality of tomographic planes of the breast M as illustrated in FIG. 6. In this case, a three-dimensional coordinate position in a three-dimensional space including the breast M is set, pixel values at corresponding pixel positions in the plurality of projection images Gi are reconstructed for the set three-dimensional coordinate position, and pixel values at the coordinate positions are calculated. A three-dimensional image of the breast M is configured by the plurality of tomographic images Dj generated by the reconstruction.

The first structure-of-interest detection unit 33 detects structures, such as abnormal shadows, specifically, important diagnostic structures, such as a calcification, a spicula, and a tumor, as the structures of interest from each of the plurality of tomographic images Dj. In this embodiment, the first structure-of-interest detection unit 33 detects the structure of interest from each of the plurality of tomographic images Dj using the above-mentioned CAD. In addition, in a case in which the structure of interest is detected by the CAD, a threshold value for determining whether or not a pixel value of a pixel included in the image is the structure of interest is used. It is assumed that the first structure-of-interest detection unit 33 detects the structure of interest using a predetermined first threshold value Th1.

The combination unit 34 generates a synthesized two-dimensional image using the plurality of tomographic images Dj. In addition, in this embodiment, the combination unit 34 generates a structure-highlighted synthesized two-dimensional image CG1.

Here, the synthesized two-dimensional image is a pseudo two-dimensional image corresponding to a simple two-dimensional image that is captured by irradiating the breast M with radiation emitted at the reference radiation source position Sc. In the first embodiment, the combination unit 34 generates the structure-highlighted synthesized two-dimensional image CG1 in which the structure of interest included in the breast M has been highlighted, using the method described in the specification of U.S. Pat. No. 8,983,156B or the specification of U.S. Pat. No. 9,792,703B.

Figure 7:
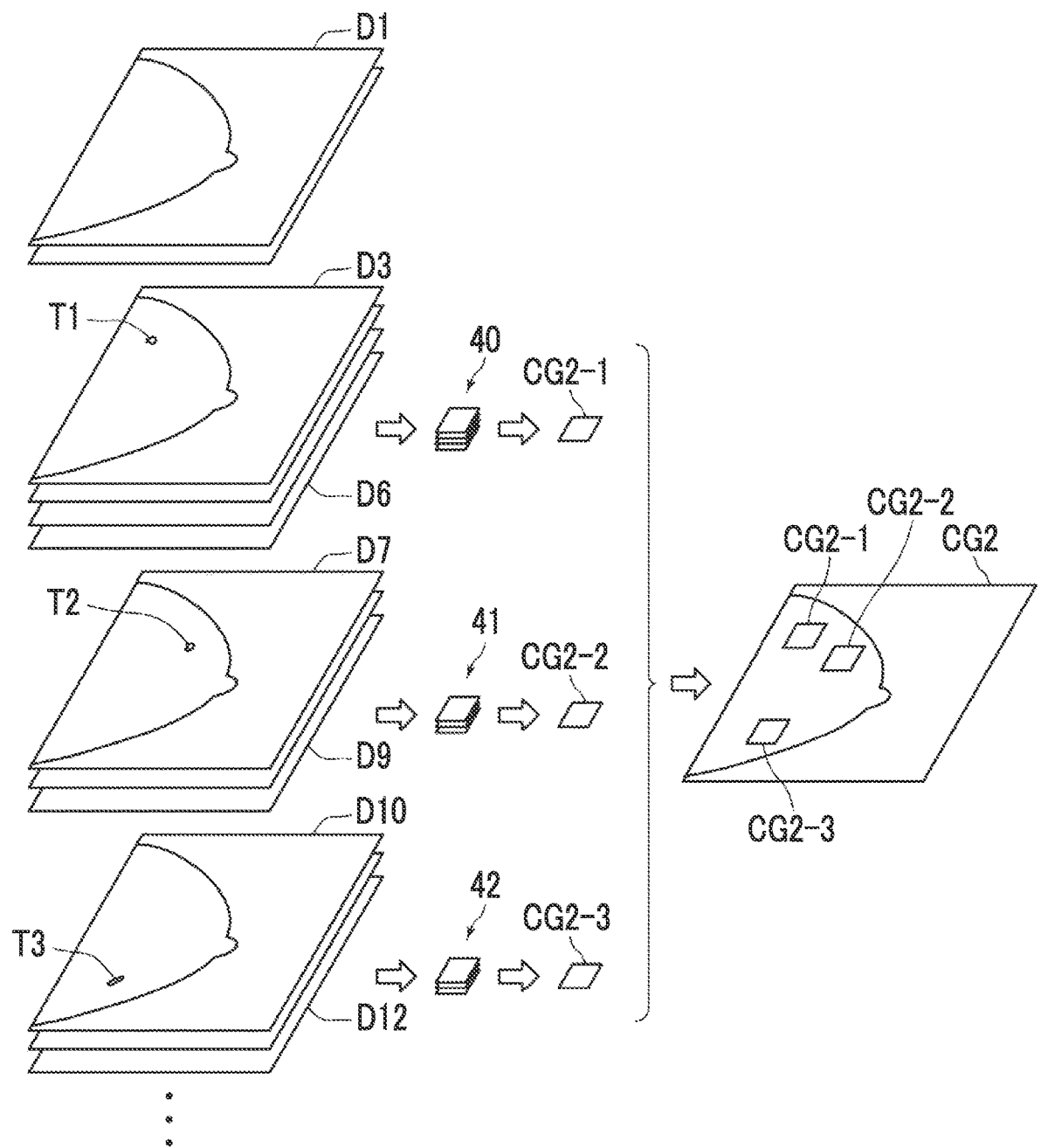
FIG. 7 is a diagram illustrating the generation of a structure-highlighted synthesized two-dimensional image.

In addition, the combination unit 34 generates the structure-highlighted synthesized two-dimensional image CG1 as follows according to the method described in the specification of U.S. Pat. No. 8,983,156B. FIG. 7 is a diagram illustrating the generation of the structure-highlighted synthesized two-dimensional image CG1. First, the combination unit 34 sets a region of interest including the structure of interest detected by the first structure-of-interest detection unit 33 in each of the plurality of tomographic images Dj. In this embodiment, it is assumed that three structures of interest T1 to T3 are detected as the structures from the plurality of tomographic images Dj. In addition, since a lesion is present in the thickness direction of the breast M, the structures of interest T1 to T3 are present across a plurality of tomographic images. For example, the structure of interest T1 is present across four tomographic images D3 to D6, the structure of interest T2 is present across three tomographic images D7 to D9, and the structure of interest T3 is present across three tomographic images D10 to D12.

The combination unit 34 sets the regions of interest including the structures of interest T1 to T3 in the plurality of tomographic images. Therefore, as illustrated in FIG. 7, a region-of-interest group 40 consisting of four regions of interest for each of the tomographic images D3 to D6 is acquired for the structure of interest T1. In addition, a region-of-interest group 41 consisting of three regions of interest for each of the tomographic images D7 to D9 is acquired for the structure of interest T2. In addition, a region-of-interest group 42 consisting of three regions of interest for each of the tomographic images D10 to D12 is acquired for the structure of interest T3.

Then, the combination unit 34 combines only the regions of interest using, for example, an addition method to generate a synthesized two-dimensional image of the regions of interest. The addition method is a method that weights and adds the pixel values of the corresponding pixels in each of the region-of-interest groups 40 to 42 along a direction from the reference radiation source position Sc to the radiation detector 15, that is, the optical axis X0 illustrated in FIG. 5 in a state in which the plurality of tomographic images Dj are stacked. In the addition method, a weight for each pixel during the weighting and addition is set to 1/x in a case in which xis the number of regions of interest included in the region-of-interest groups 40 to 42. Further, a method for generating the synthesized two-dimensional image of the regions of interest is not limited to the addition method, and a known technique, such as an averaging method, a minimum intensity projection method, or a maximum intensity projection method, can be applied. As a result, the combination unit 34 generates region-of-interest synthesized two-dimensional images CG2-1, CG2-2, and CG2-3 for the region-of-interest groups 40 to 42, respectively.

Further, the combination unit 34 combines the region-of-interest synthesized two-dimensional images CG2-1, CG2-2, and CG2-3 with a predetermined two-dimensional image to generate the structure-highlighted synthesized two-dimensional image CG1. A projection image acquired in a case in which the radiation source 16 is at the reference radiation source position Sc may be used as the predetermined two-dimensional image. In addition, a simple two-dimensional image separately acquired by simple imaging may be used.

Further, the combination unit 34 may generate the structure-highlighted synthesized two-dimensional image CG1, in which structures have been highlighted, by performing combination on the basis of the tomographic images in which the structures have been detected using the method described in the specification of U.S. Pat. No. 9,792,703B instead of the method described in the specification of U.S. Pat. No. 8,983,156B. In addition, the structure of interest may not be detected by the first structure-of-interest detection unit 33. In this case, the combination unit 34 may generate a synthesized two-dimensional image using, for example, the method described in JP2014-128716A.

The second structure-of-interest detection unit 35 detects structures, such as abnormal shadows, specifically, important diagnostic structures, such as a calcification, a spicula, and a tumor, as the structures of interest from the plurality of tomographic images Dj or the synthesized two-dimensional image CG1. In this embodiment, the second structure-of-interest detection unit 35 detects the structures of interest from each of the plurality of tomographic images Dj or the synthesized two-dimensional image CG1 using the above-mentioned CAD, similarly to the first structure-of-interest detection unit 33. In addition, a second threshold value Th2 used in a case in which the second structure-of-interest detection unit 35 detects the structure of interest is set to a value smaller than the first threshold value Th1. Therefore, the second structure-of-interest detection unit 35 has a higher structure-of-interest detection sensitivity than the first structure-of-interest detection unit 33. In addition, the detection of the structure of interest from the plurality of tomographic images Dj means that the structure of interest is detected from each of the plurality of tomographic images Dj.

The setting control unit 36 sets at least some of the plurality of tomographic images Dj as the non-storage-required images and sets the structure-highlighted synthesized two-dimensional image CG1 as the storage-required image in a case in which the second structure-of-interest detection unit 35 does not detect the structure of interest from the plurality of tomographic images Dj or the synthesized two-dimensional image CG1. On the other hand, in a case in which the structure of interest is detected, the setting control unit 36 sets at least some of the plurality of tomographic images Dj and the structure-highlighted synthesized two-dimensional image CG1 as the storage-required images. The at least some of the plurality of tomographic images Dj may be all of the plurality of tomographic images Dj or may be one or more tomographic images among the plurality of tomographic images Dj. Some of the plurality of tomographic images Dj may be the tomographic images in which the structure of interest has been detected by the first structure-of-interest detection unit 33 or the second structure-of-interest detection unit 35. Further, the tomographic images designated by the operator may be used as some of the plurality of tomographic images Dj.

In addition, the setting control unit 36 sets a flag indicating that the image is the storage-required image in a header of an image file of the image set as the storage-required image to set that the image is the storage-required image. Further, the setting control unit 36 may generate a database for the plurality of tomographic images Dj and the synthesized two-dimensional image CG1 in the storage 23 and assign "1" to the flag of the database for the image set as the storage-required image. Furthermore, a flag "0" is set to a tomographic image that is not set as the storage-required image, that is, a tomographic image that is set as the non-storage-required image. The flag corresponds to information indicating the detection result of the structure of interest.

The storage control unit 37 stores the image set as the storage-required image in the storage 23. That is, in a case in which the setting control unit 36 sets the synthesized two-dimensional image CG1 as the storage-required image, the storage control unit 37 stores the synthesized two-dimensional image CG1 in the storage 23. On the other hand, in a case in which the setting control unit 36 sets at least some of the plurality of tomographic images Dj and the synthesized two-dimensional image CG1 as the storage-required images, the storage control unit 37 stores the at least some of the plurality of tomographic images Dj and the synthesized two-dimensional image CG1 in the storage 23. In addition, the image set as the non-storage-required image is not stored in the storage 23.

The transmission control unit 38 transmits the image set as the storage-required images from the communication I/F 24 to the PACS 7 through the network 5. That is, in a case in which the setting control unit 36 sets the synthesized two-dimensional image CG1 as the storage-required image, the transmission control unit 38 transmits the synthesized two-dimensional image CG1 to the PACS 7. On the other hand, in a case in which the setting control unit 36 sets at least some of the plurality of tomographic images Dj and the synthesized two-dimensional image CG1 as the storage-required images, the transmission control unit 38 transmits the at least some of the plurality of tomographic images Dj and the synthesized two-dimensional image CG1 to the PACS 7. The transmitted image is stored in the PACS 7 and is further transmitted to the image interpretation terminal 8 as needed. The image set as the non-storage-required image is not transmitted to the PACS 7.

Figure 8:
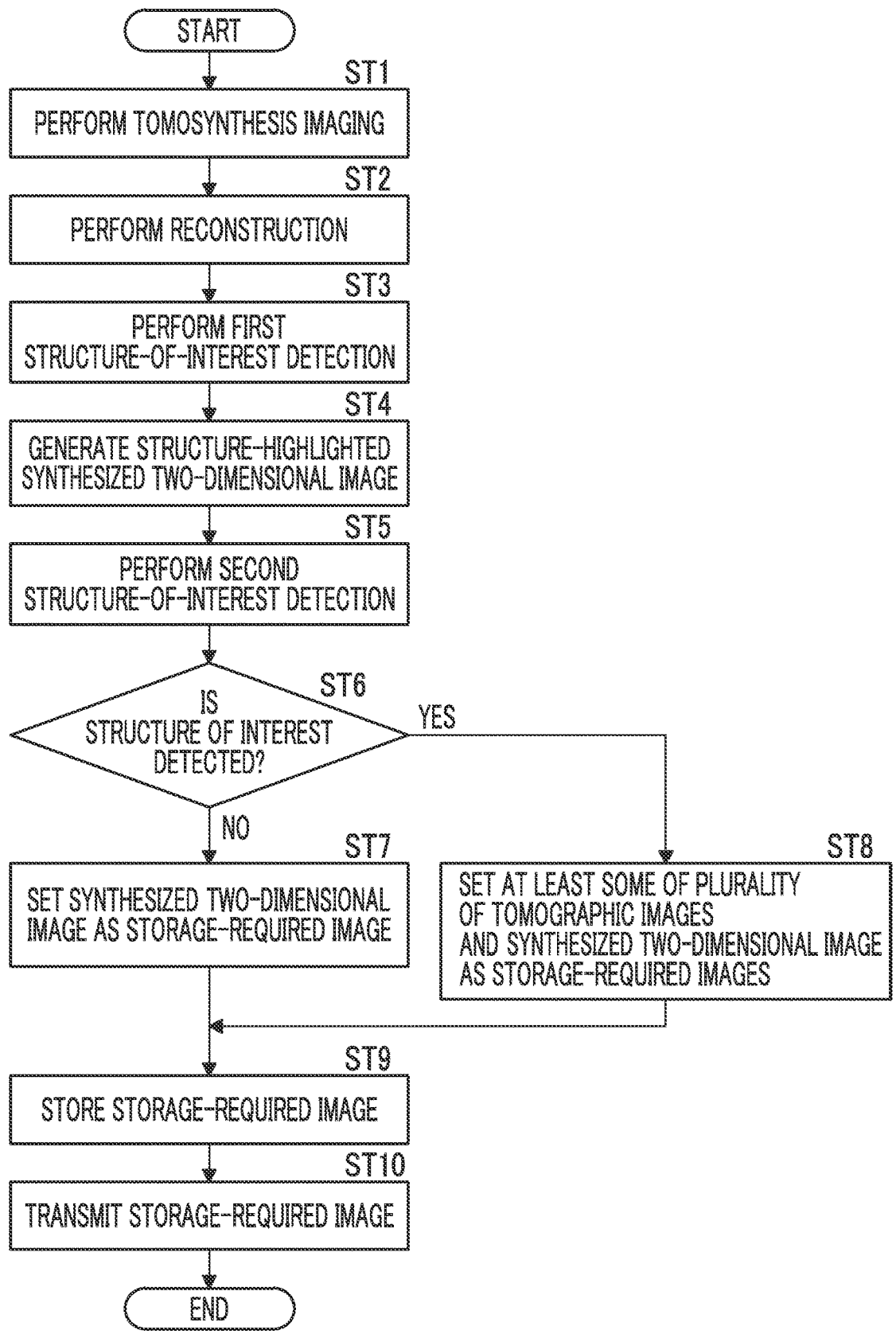
FIG. 8 is a flowchart illustrating a process performed in the first embodiment.

Next, a process performed in the first embodiment will be described. FIG. 8 is a flowchart illustrating the process performed in the first embodiment. First, the process is started by the input of an imaging instruction by the operator, and the image acquisition unit 31 instructs the mammography apparatus 10 to perform tomosynthesis imaging. Then, the mammography apparatus 10 performs the tomosynthesis imaging on the breast M (Step ST1). A plurality of projection images Gi are acquired by the tomosynthesis imaging. Then, the reconstruction unit 32 reconstructs the plurality of projection images Gi acquired by the tomosynthesis imaging (Step ST2). Then, a plurality of tomographic images Dj are generated. Then, the first structure-of-interest detection unit 33 detects the structure of interest from each of the plurality of tomographic images Dj (first structure-of-interest detection: Step ST3).

Then, the combination unit 34 generates the structure-highlighted synthesized two-dimensional image CG1 using the structure of interest detected by the first structure-of-interest detection unit 33 (Step ST4). Then, the second structure-of-interest detection unit 35 detects the structure of interest from the plurality of tomographic images Dj or the synthesized two-dimensional image CG1 (second structure-of-interest detection: Step ST5).

Then, the setting control unit 36 sets the storage-required image. That is, the setting control unit 36 determines whether or not the second structure-of-interest detection unit 35 detects the structure of interest from the plurality of tomographic images Dj or the synthesized two-dimensional image CG1 (Step ST6). In a case in which the determination result in Step ST6 is "No", the setting control unit 36 sets at least some of the plurality of tomographic images Dj as the non-storage-required images and sets the synthesized two-dimensional image CG1 as the storage-required image (Step ST7). On the other hand, in a case in which the determination result in Step ST6 is "Yes", the setting control unit 36 sets at least some of the plurality of tomographic images Dj and the synthesized two-dimensional image CG1 as the storage-required images (Step ST8). In addition, in the following description, it is assumed that only the step of setting the image as the storage-required image is described in the flowchart. Then, the storage control unit 37 stores the image set as the storage-required image in the storage 23 (Step ST9), and the transmission control unit 38 transmits the image set as the storage-required image to the PACS 7 (Step ST10). Then, the process ends. The storage-required image transmitted from the console 2 is stored in the PACS 7.

Here, the structure-highlighted synthesized two-dimensional image CG1 includes information of the structure of interest included in the tomographic images Dj since the structure of interest detected from the plurality of tomographic images Dj is highlighted. Further, in a case in which the structure of interest is not detected from the structure-highlighted synthesized two-dimensional image CG1, it is considered that the plurality of tomographic images Dj do not include the structure of interest. Therefore, even in a case in which there is no tomographic image Dj, it may be possible to make a diagnosis using only the structure-highlighted synthesized two-dimensional image CG1. In this case, there is little need to store or transmit the plurality of tomographic images Dj. On the other hand, in a case in which the structure of interest is detected from the structure-highlighted synthesized two-dimensional image CG1 or the tomographic images Dj, it is necessary to interpret in detail whether or not the structure of interest is a lesion, using the tomographic images Dj. In particular, in a case in which the structure-highlighted synthesized two-dimensional image CG1 includes the structure of interest, a lesion structure may be represented in a specific tomographic plane among a plurality of tomographic planes indicated by each of the plurality of tomographic images Dj. In addition, normal structures in a plurality of tomographic planes may overlap each other and look like a lesion. In this case, it is possible to interpret the tomographic images to determine that the structure is not a lesion.

In the first embodiment, in a case in which the structure of interest is not detected from the plurality of tomographic images Dj or the synthesized two-dimensional image CG1, at least some of the plurality of tomographic images Dj are set as the non-storage-required images, and the structure-highlighted synthesized two-dimensional image CG1 is set as the storage-required image. Further, in a case in which the structure of interest is detected, at least some of the plurality of tomographic images Dj and the synthesized two-dimensional image CG1 are set as the storage-required images. Therefore, since only the storage-required images are stored or transmitted, it is possible to reduce the number of images to be stored or transmitted while storing or transmitting the images required for diagnosis, as compared to a case in which all of the plurality of tomographic images Dj are stored or transmitted. As a result, according to this embodiment, it is possible to further reduce the cost for storage or transmission.

Furthermore, in a case in which the structure of interest is detected, at least some of the plurality of tomographic images Dj are set as the storage-required images. Therefore, it is possible to interpret images using at least some of the plurality of tomographic images Dj together with the structure-highlighted synthesized two-dimensional image CG1. Therefore, it is possible to interpret the structure of interest in detail using the tomographic images Dj.

In a case in which the structure of interest is detected, only some tomographic images, such as the tomographic images in which the structure of interest has been detected, among the plurality of tomographic images Dj are set as the storage-required images. Therefore, it is possible to reduce the number of images to be stored or transmitted, as compared to a case in which all of the tomographic images are stored or transmitted. Therefore, it is possible to further reduce the cost for storage or transmission.

Further, since the flag indicating the storage-required image is set in the header of the image file of the image in which the structure of interest has been detected, information indicating the detection result of the structure of interest is stored in the storage 23 or transmitted to the PACS 7 together with the image set as the storage-required image. Therefore, in a case in which the structure-highlighted synthesized two-dimensional image CG1 is interpreted and includes the structure of interest suspected to be a lesion, it is possible to interpret the images with reference to the tomographic images Dj including the structure of interest on the basis of the flag.

Figure 9:
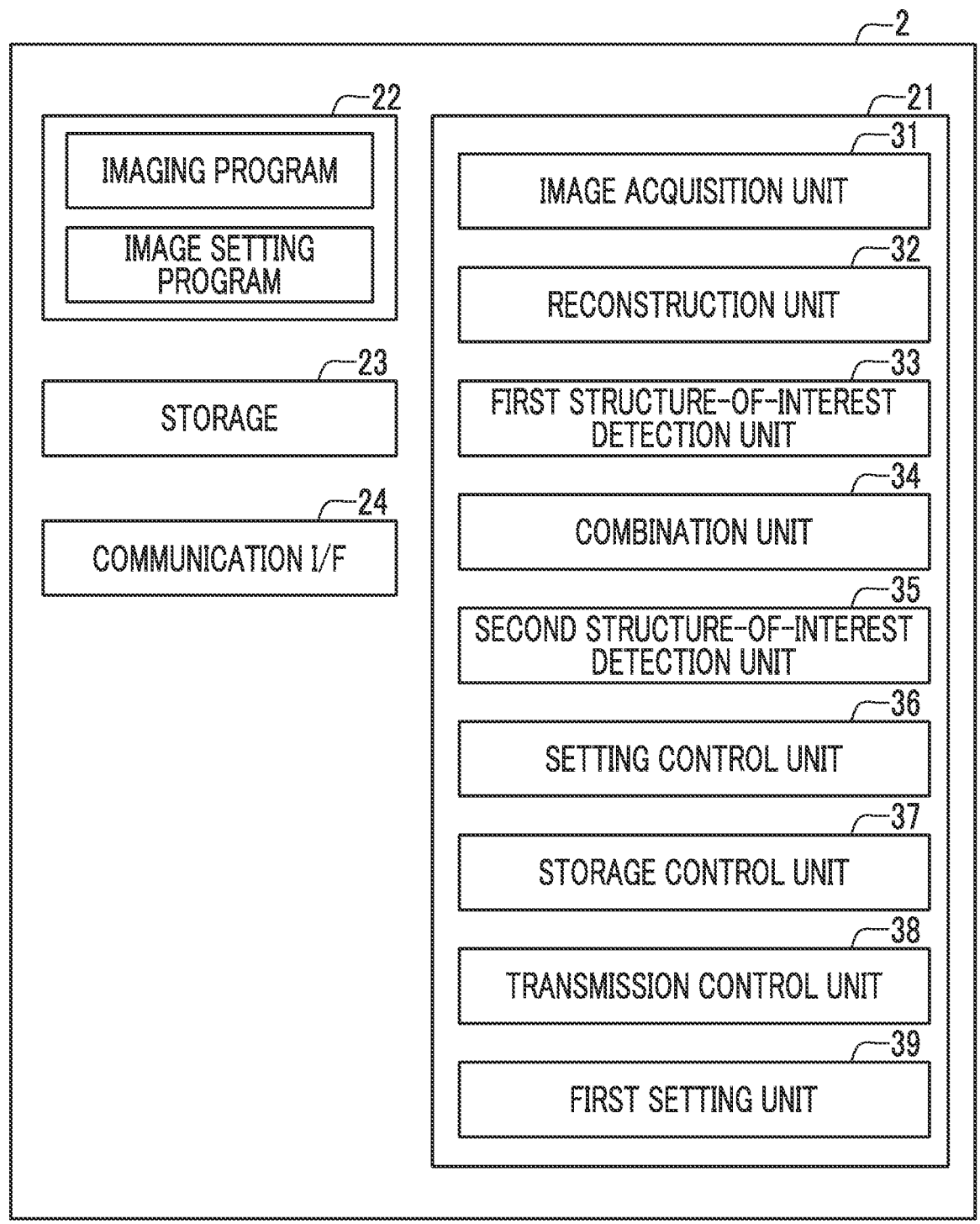
FIG. 9 is a diagram schematically illustrating a configuration of an image setting device according to a second embodiment that is implemented by installing the imaging program and the image setting program in the computer constituting the console.

Next, a second embodiment of the present disclosure will be described. FIG. 9 is a diagram schematically illustrating the configuration of an image setting device according to the second embodiment of the present disclosure that is implemented by installing the imaging program and the image setting program in the computer constituting the console. In addition, in FIG. 9, the same components as those in FIG. 4 are denoted by the same reference numerals, and the detailed description thereof will not be repeated. The second embodiment differs from the first embodiment in that the image setting device further comprises a first setting unit 39 that receives a setting of whether or not to determine at least some of the plurality of tomographic images Dj as the storage-required images in a case in which the second structure-of-interest detection unit 35 does not detect the structure of interest from the plurality of tomographic images Dj or the synthesized two-dimensional image CG1 and, in a case in which the structure of interest is not detected from the plurality of tomographic images Dj or the synthesized two-dimensional image CG1 and the first setting unit 39 receives the setting of whether or not to determine at least some of the plurality of tomographic images Dj as the storage-required images, the setting control unit 36 sets at least some of the plurality of tomographic images Dj and the synthesized two-dimensional image CG1 as the storage-required images.

Figure 10:
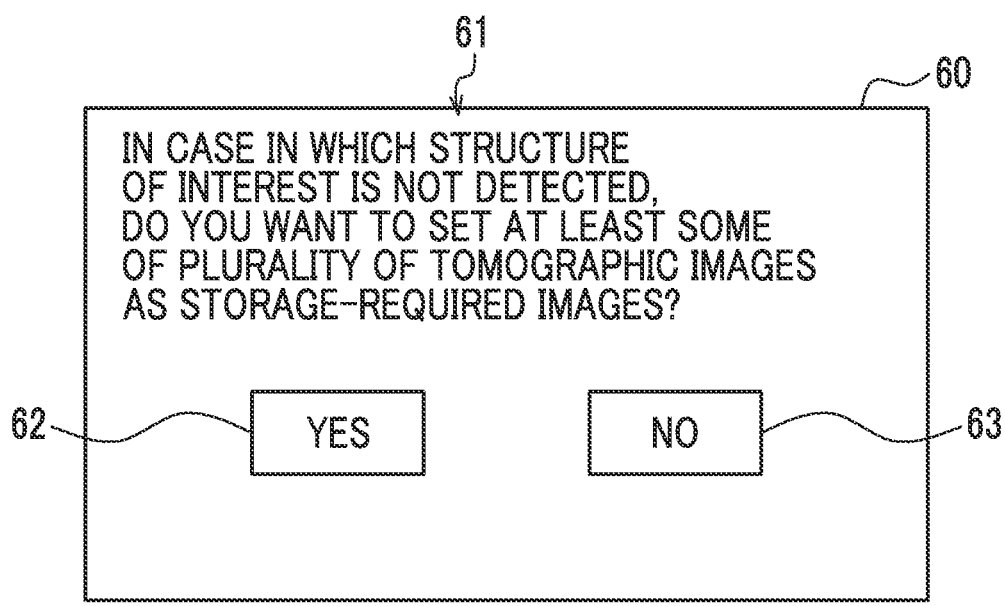
FIG. 10 is a diagram illustrating a setting screen for receiving a setting of whether or not to determine at least some of a plurality of tomographic images as storage-required images in a case in which a structure of interest is not detected.

The first setting unit 39 receives the setting of whether or not to determine at least some of the plurality of tomographic images Dj as the storage-required images in a case in which the second structure-of-interest detection unit 35 does not detect the structure of interest from the plurality of tomographic images Dj or the synthesized two-dimensional image CG1. The reception of the setting of whether or not to determine at least some of the plurality of tomographic images Dj as the storage-required images may be performed by an instruction that is input from the input device 4 by the operator through a setting screen displayed on the display 3. FIG. 10 is a diagram illustrating a setting screen for receiving the setting of whether or not to determine at least some of the plurality of tomographic images Dj as the storage-required images in a case in which the structure of interest is not detected. As illustrated in FIG. 10, the following are displayed on a setting screen 60: a text 61 of "In a case in which the structure of interest is not detected, do you want to set at least some of the plurality of tomographic images as the storage-required images?"; a YES button 62 that is selected in a case in which the tomographic images are set as the storage-required images; and a NO button 63 that is selected in a case in which the tomographic images are not set as the storage-required images. The operator can select the YES button 62 or the NO button 63 using the input device 4 to set whether or not to determine at least some of the plurality of tomographic images Dj as the storage-required images. The result of the setting by the first setting unit 39 is stored in the storage 23.

In addition, the reception of the setting of whether or not to determine at least some of the plurality of tomographic images Dj as the storage-required images can be performed at any timing. For example, the setting can be performed before the start of imaging, before the start of the reconstruction process, before the first structure-of-interest detection process, before the structure-highlighted synthesized two-dimensional image generation process, before the second structure-of-interest detection process, or before it is determined whether or not the second structure-of-interest detection unit 35 detects the structure of interest. In this embodiment, it is assumed that the reception of the setting of whether or not to determine at least some of the plurality of tomographic images Dj as the storage-required images is performed before it is determined whether or not the second structure-of-interest detection unit 35 detects the structure of interest.

Figure 11:
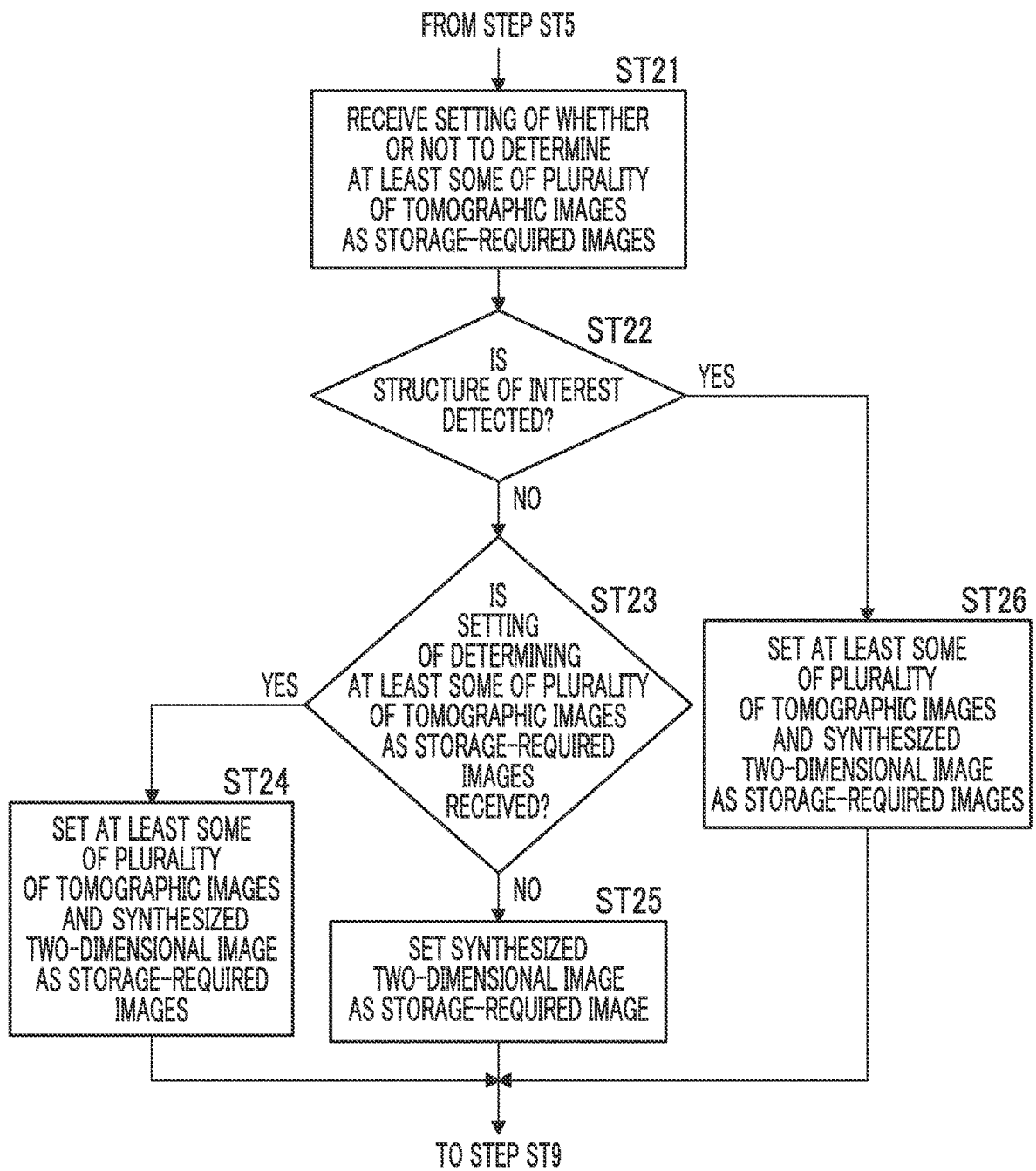
FIG. 11 is a flowchart illustrating a process performed in the second embodiment.

Next, a process performed in the second embodiment will be described. FIG. 11 is a flowchart illustrating the process performed in the second embodiment. In addition, in the second embodiment, since the processes up to the second structure-of-interest detection process are the same as the processes from Step ST1 to Step ST5 in the processes according to the first embodiment illustrated in FIG. 8, the processes after Step ST5 in FIG. 8 will be described.

In a case in which the second structure-of-interest detection unit 35 performs the process of detecting the structure of interest from the plurality of tomographic images Dj or the synthesized two-dimensional image CG1 and does not detect the structure of interest, the first setting unit 39 receives the setting of whether or not to determine at least some of the plurality of tomographic images Dj as the storage-required images on the basis of the instruction from the operator (Step ST21).

Then, the setting control unit 36 sets the storage-required image. That is, the setting control unit 36 determines whether or not the second structure-of-interest detection unit 35 detects the structure of interest from the plurality of tomographic images Dj or the synthesized two-dimensional image CG1 (Step ST22). In a case in which the determination result in Step ST22 is "No", the setting control unit 36 determines whether or not the setting of determining at least some of the plurality of tomographic images Dj as the storage-required images is received (Step ST23). In a case in which the determination result in Step ST23 is "Yes", the setting control unit 36 sets at least some of the plurality of tomographic images Dj and the synthesized two-dimensional image CG1 as the storage-required images (Step ST24). In a case in which the determination result in Step ST23 is "No", the setting control unit 36 sets at least some of the plurality of tomographic images Dj as the non-storage-required images and sets the synthesized two-dimensional image CG1 as the storage-required image (Step ST25).

In a case in which the determination result in Step ST22 is "Yes", that is, in a case in which the structure of interest is detected from the plurality of tomographic images Dj or the synthesized two-dimensional image CG1, the setting control unit 36 sets at least some of the plurality of tomographic images Dj and the synthesized two-dimensional image CG1 as the storage-required images (Step ST26). In addition, since the processes after Steps ST24, ST25, and ST26 are the same as the processes after Step ST9 illustrated in FIG. 8, the detailed description thereof will not be repeated here.

As described above, in the second embodiment, in a case in which the structure of interest is not detected from the plurality of tomographic images Dj or the synthesized two-dimensional image CG1, whether or not to determine at least some of the plurality of tomographic images Dj as the storage-required images is set. Therefore, it is also possible to respond to a case in which the structure of interest is not detected from the plurality of tomographic images Dj or the synthesized two-dimensional image CG1 and there is a request to store or transmit at least some of the plurality of tomographic images Dj.

Figure 12:
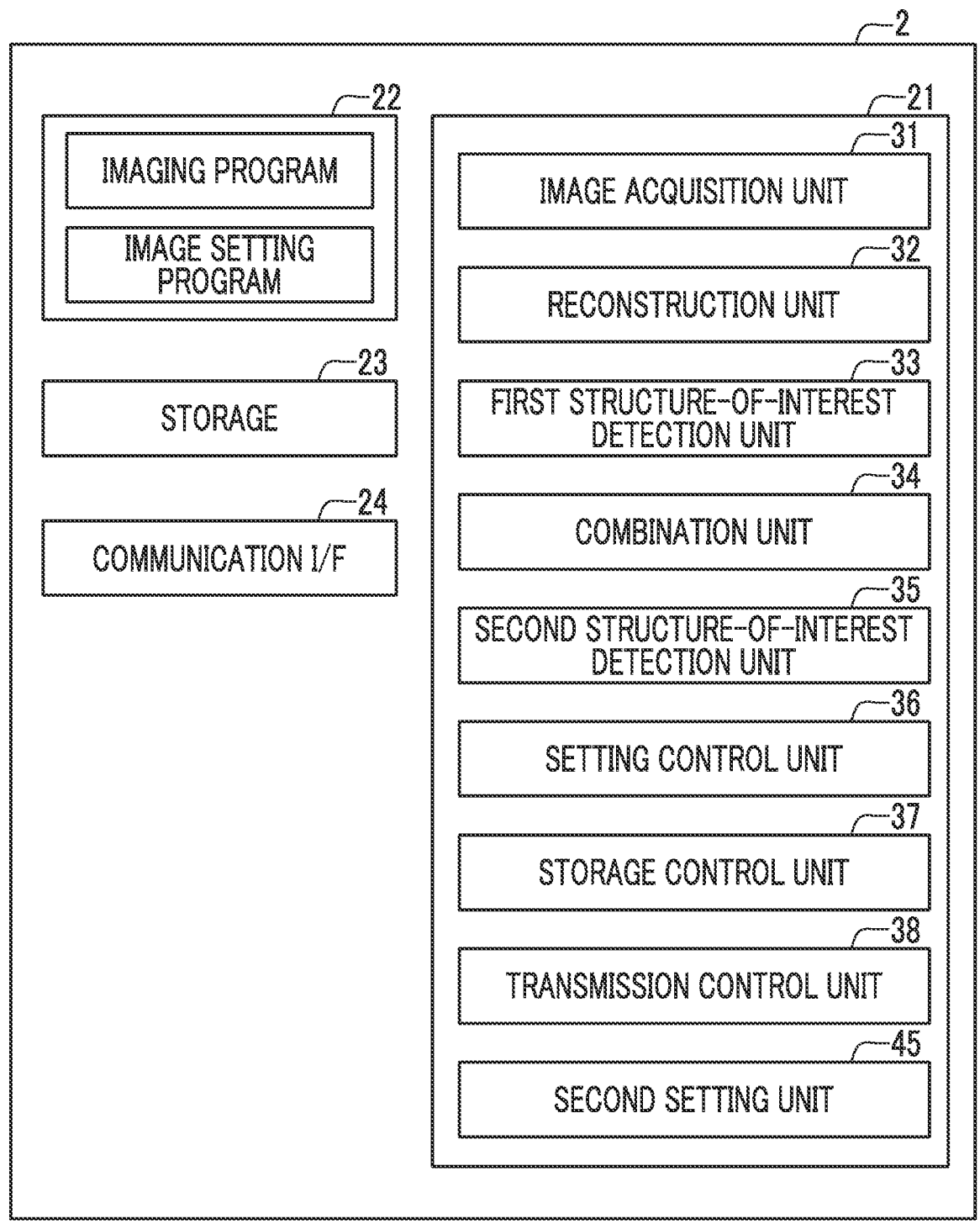
FIG. 12 is a diagram schematically illustrating a configuration of an image setting device according to a third embodiment that is implemented by installing the imaging program and the image setting program in the computer constituting the console.

Next, a third embodiment of the present disclosure will be described. FIG. 12 is a diagram schematically illustrating the configuration of an image setting device according to the third embodiment of the present disclosure that is implemented by installing the imaging program and the image setting program in the computer constituting the console. In addition, in FIG. 12, the same components as those in FIG. 4 are denoted by the same reference numerals, and the detailed description thereof will not be repeated. The third embodiment differs from the first embodiment in that the image setting device further comprises a second setting unit 45 that receives a setting of whether or not to determine at least some of the plurality of tomographic images Dj as the storage-required images in a case in which the second structure-of-interest detection unit 35 detects the structure of interest from the plurality of tomographic images Dj or the synthesized two-dimensional image CG1 and the setting control unit 36 sets at least some of the plurality of tomographic images Dj as the storage-required images only in a case in which the structure of interest is detected from the plurality of tomographic images Dj or the synthesized two-dimensional image CG1 and the second setting unit 45 receives the setting of determining at least some of the plurality of tomographic images Dj as the storage-required images.

Figure 13:
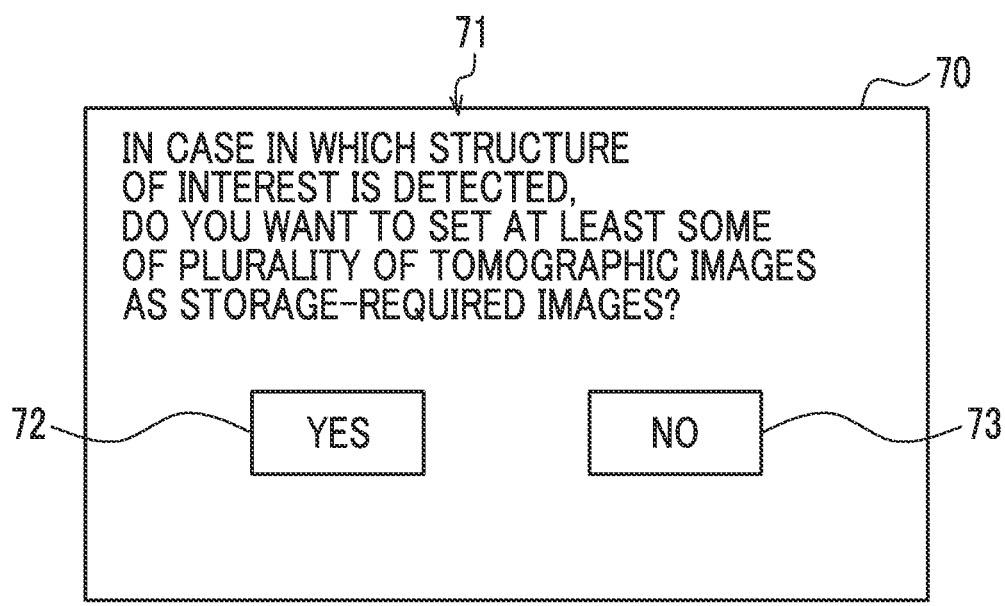
FIG. 13 is a diagram illustrating a setting screen for receiving a setting of whether or not to determine at least some of the plurality of tomographic images as the storage-required images in a case in which the structure of interest is detected.

The second setting unit 45 receives the setting of whether or not to determine at least some of the plurality of tomographic images Dj as the storage-required images in a case in which the second structure-of-interest detection unit 35 detects the structure of interest from the plurality of tomographic images Dj or the synthesized two-dimensional image CG1. The reception of the setting of whether or not to determine at least some of the plurality of tomographic images Dj as the storage-required images may be performed by an instruction that is input from the input device 4 by the operator through a setting screen displayed on the display 3. FIG. 13 is a diagram illustrating a setting screen for receiving a setting of whether or not to determine at least some of the plurality of tomographic images Dj as the storage-required images in a case in which the structure of interest is detected. As illustrated in FIG. 13, the following are displayed on a setting screen 70: a text 71 of "In a case in which the structure of interest is detected, do you want to set at least some of the plurality of tomographic images as the storage-required images?"; a YES button 72 that is selected in a case in which the tomographic images are set as the storage-required images; and a NO button 73 that is selected in a case in which the tomographic images are not set as the storage-required images. The operator can select the YES button 72 or the NO button 73 using the input device 4 to set whether or not to determine at least some of the plurality of tomographic images Dj as the storage-required images. The result of the setting by the second setting unit 45 is stored in the storage 23.

In addition, the reception of the setting of whether or not to determine at least some of the plurality of tomographic images Dj as the storage-required images can be performed at any timing. For example, the setting can be performed before the start of imaging, before the start of the reconstruction process, before the first structure-of-interest detection process, before the structure-highlighted synthesized two-dimensional image generation process, before the second structure-of-interest detection process, or before it is determined whether or not the second structure-of-interest detection unit 35 detects the structure of interest. In this embodiment, it is assumed that the reception of the setting of whether or not to set at least some of the plurality of tomographic images Dj as the storage-required images is performed before it is determined whether or not the second structure-of-interest detection unit 35 detects the structure of interest.

Figure 14:
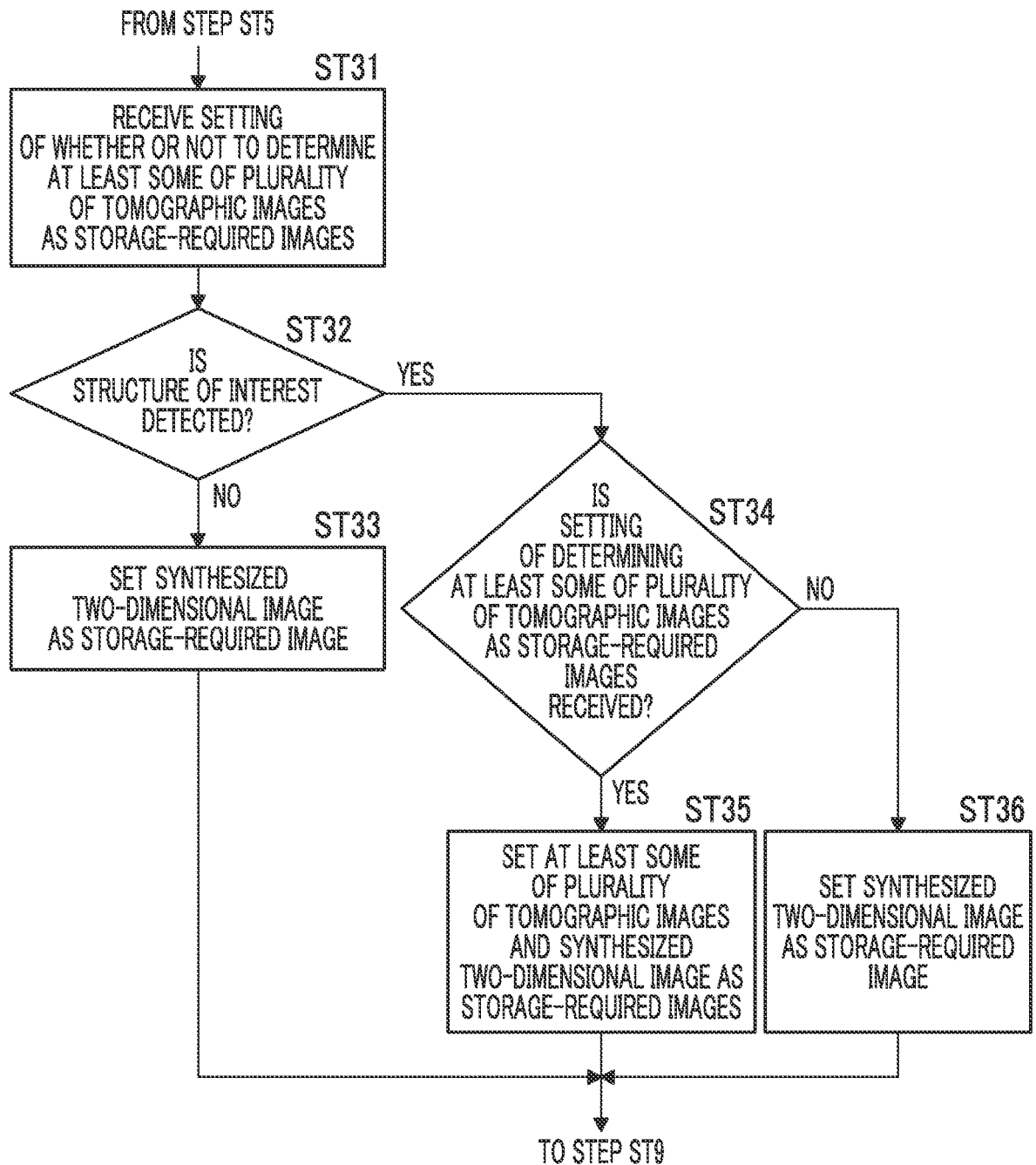
FIG. 14 is a flowchart illustrating a process performed in a third embodiment.

Next, a process performed in the third embodiment will be described. FIG. 14 is a flowchart illustrating the process performed in the third embodiment. In addition, in the third embodiment, since the processes up to the second structure-of-interest detection process are the same as the processes from Step ST1 to Step ST5 in the processes according to the first embodiment illustrated in FIG. 8, the processes after Step ST5 in FIG. 8 will be described.

In a case in which the second structure-of-interest detection unit 35 performs the process of detecting the structure of interest from the plurality of tomographic images Dj or the synthesized two-dimensional image CG1 and detects the structure of interest from the plurality of tomographic images Dj, the second setting unit 45 receives the setting of whether or not to determine at least of some of the plurality of tomographic images Dj as the storage-required images on the basis of the instruction from the operator (Step ST31). Then, the setting control unit 36 sets the storage-required image. That is, the setting control unit 36 determines whether or not the second structure-of-interest detection unit 35 detects the structure of interest from the plurality of tomographic images Dj or the synthesized two-dimensional image CG1 (Step ST32). In a case in which the determination result in Step ST32 is "No", the setting control unit 36 sets at least some of the plurality of tomographic images Dj as the non-storage-required images and sets the synthesized two-dimensional image CG1 as the storage-required image (Step ST33).

In a case in which the determination result in Step ST32 is "Yes", that is, in a case in which the structure of interest is detected from the plurality of tomographic images Dj or the synthesized two-dimensional image CG1, the setting control unit 36 determines whether or not the setting of determining at least some of the plurality of tomographic images Dj as the storage-required images is received (Step ST34). In a case in which the determination result in Step ST34 is "Yes", the setting control unit 36 sets at least some of the plurality of tomographic images Dj and the synthe- sized two-dimensional image CG1 as the storage-required images (Step ST35). In a case in which the determination result in Step ST34 is "No", the setting control unit 36 sets at least some of the plurality of tomographic images Dj as the non-storage-required images and sets the synthesized two-dimensional image CG1 as the storage-required image (Step ST36). In addition, since the processes after Steps ST33, ST35, and ST36 are the same as the processes after Step ST9 illustrated in FIG. 8, the detailed description thereof will not be repeated here.

As described above, in the third embodiment, in a case in which the structure of interest is detected from the plurality of tomographic images Dj or the synthesized two-dimensional image CG1, whether or not to determine at least some of the plurality of tomographic images Dj as the storage-required images is set. Therefore, it is also possible to respond to a case in which the structure of interest is detected from the plurality of tomographic images Dj or the synthesized two-dimensional image CG1 and a case in which there is a request not to store or transmit at least some of the plurality of tomographic images Dj.

In the third embodiment, the first setting unit 39 may be provided as in the second embodiment. In this case, in the processes after the determination result in Step ST32 is "No" in the flowchart illustrated in FIG. 14, the processes after Step ST23 in the flowchart illustrated in FIG. 11 are performed.

Next, a fourth embodiment of the present disclosure will be described. In addition, the configuration of an image setting device according to the fourth embodiment is the same as the configuration of the image setting device according to the first embodiment except only the process to be performed. Therefore, the detailed description of the device will not be repeated here. In the first embodiment, in a case in which the second structure-of-interest detection unit 35 does not detect the structure of interest from the plurality of tomographic images Dj or the synthesized two-dimensional image CG1, at least some of the plurality of tomographic images Dj are set as the non-storage-required images, and the synthesized two-dimensional image CG1 is set as the storage-required image. In a case in which the structure of interest is detected, at least some of the plurality of tomographic images Dj and the synthesized two-dimensional image CG1 are set as the storage-required images. The fourth embodiment differs from the first embodiment in that at least some of the plurality of tomographic images Dj and the synthesized two-dimensional image CG1 are set as the storage-required images in a case in which the second structure-of-interest detection unit 35 does not detect the structure of interest from the plurality of tomographic images Dj or the synthesized two-dimensional image CG1, and at least some of the plurality of tomographic images Dj are set as the non-storage-required images and only the synthesized two-dimensional image CG1 is set as the storage-required image in a case in which the structure of interest is detected.

Figure 15:
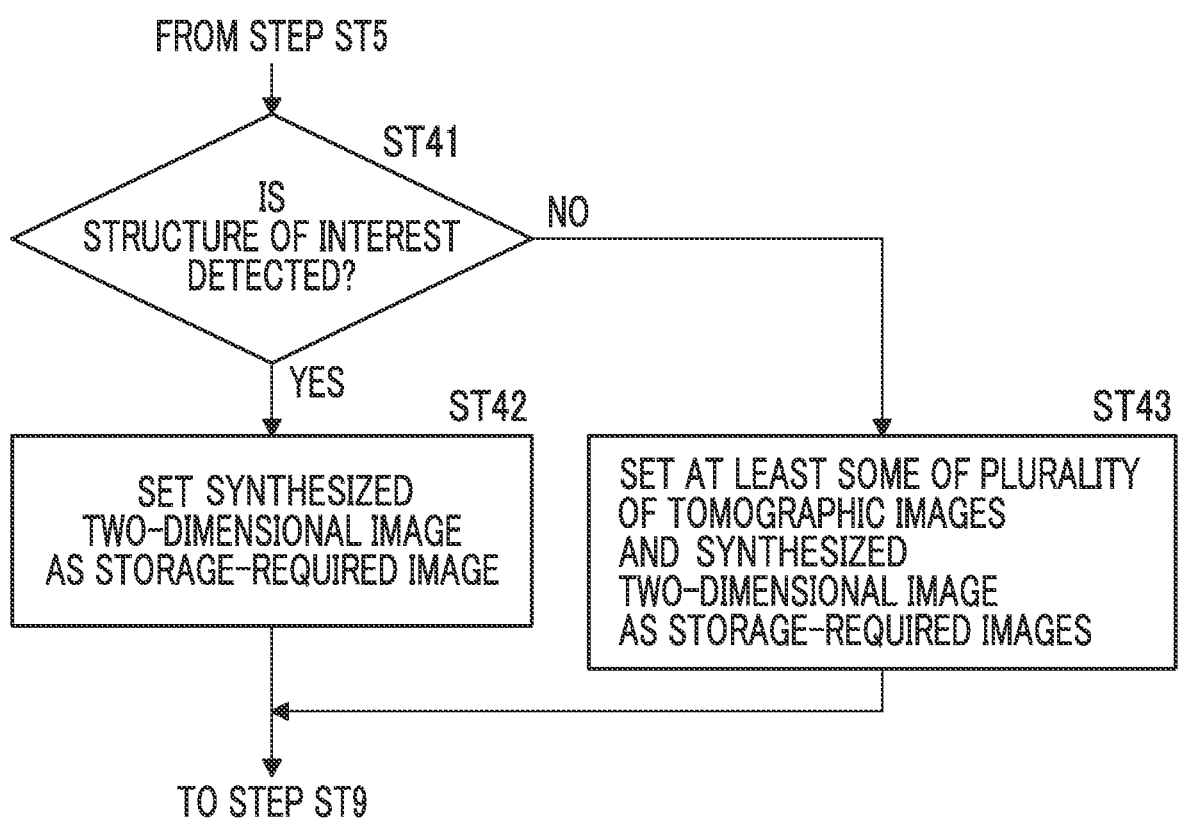
FIG. 15 is a flowchart illustrating a process performed in a fourth embodiment.

Next, a process performed in the fourth embodiment will be described. FIG. 15 is a flowchart illustrating the process performed in the fourth embodiment. In addition, in the fourth embodiment, since the processes up to the second structure-of-interest detection process are the same as the processes from Step ST1 to Step ST5 in the processes according to the first embodiment illustrated in FIG. 8, the processes after Step ST5 in FIG. 8 will be described.

In a case in which the second structure-of-interest detection unit 35 performs the process of detecting the structure of interest from the plurality of tomographic images Dj or the synthesized two-dimensional image CG1, the setting control unit 36 sets the storage-required images. That is, the setting control unit 36 determines whether or not the second structure-of-interest detection unit 35 detects the structure of interest from the plurality of tomographic images Dj or the synthesized two-dimensional image CG1 (Step ST41). In a case in which the determination result in Step ST41 is "Yes", the setting control unit 36 sets at least some of the plurality of tomographic images Dj as the non-storage-required images and sets the synthesized two-dimensional image CG1 as the storage-required image (Step ST42). On the other hand, in a case in which the determination result in Step ST41 is "No", the setting control unit 36 sets at least some of the plurality of tomographic images Dj and the synthesized two-dimensional image CG1 as the storage-required images (Step ST43). In addition, since the processes after Steps ST42 and ST43 are the same as the processes after Step ST9 illustrated in FIG. 8, the detailed description thereof will not be repeated here.

Here, in the structure-highlighted synthesized two-dimensional image CG1, the structure of interest detected from the plurality of tomographic images Dj has been highlighted. Therefore, in a case in which the structure of interest is detected from the plurality of tomographic images Dj or the structure-highlighted synthesized two-dimensional image CG1, the information of the structure of interest included in the plurality of tomographic images Dj is represented by the structure-highlighted synthesized two-dimensional image CG1. In this case, there is little need to store or transmit the plurality of tomographic images Dj.

In the fourth embodiment, in a case in which the structure of interest is not detected from the plurality of tomographic images Dj or the structure-highlighted synthesized two-dimensional image CG1, at least some of the plurality of tomographic images Dj and the structure-highlighted synthesized two-dimensional image CG1 are set as the storage-required images. Further, in a case in which the structure of interest is detected, at least some of the plurality of tomographic images Dj are set as the non-storage-required images, and the synthesized two-dimensional image CG1 is set as the storage-required image. Therefore, since only the storage-required images are stored or transmitted, it is possible to reduce the number of images to be stored or transmitted while storing or transmitting the images required for diagnosis, as compared to a case in which all of the plurality of tomographic images Dj are stored or transmitted. As a result, according to this embodiment, it is possible to further reduce a cost for storage or transmission.

Figure 16:
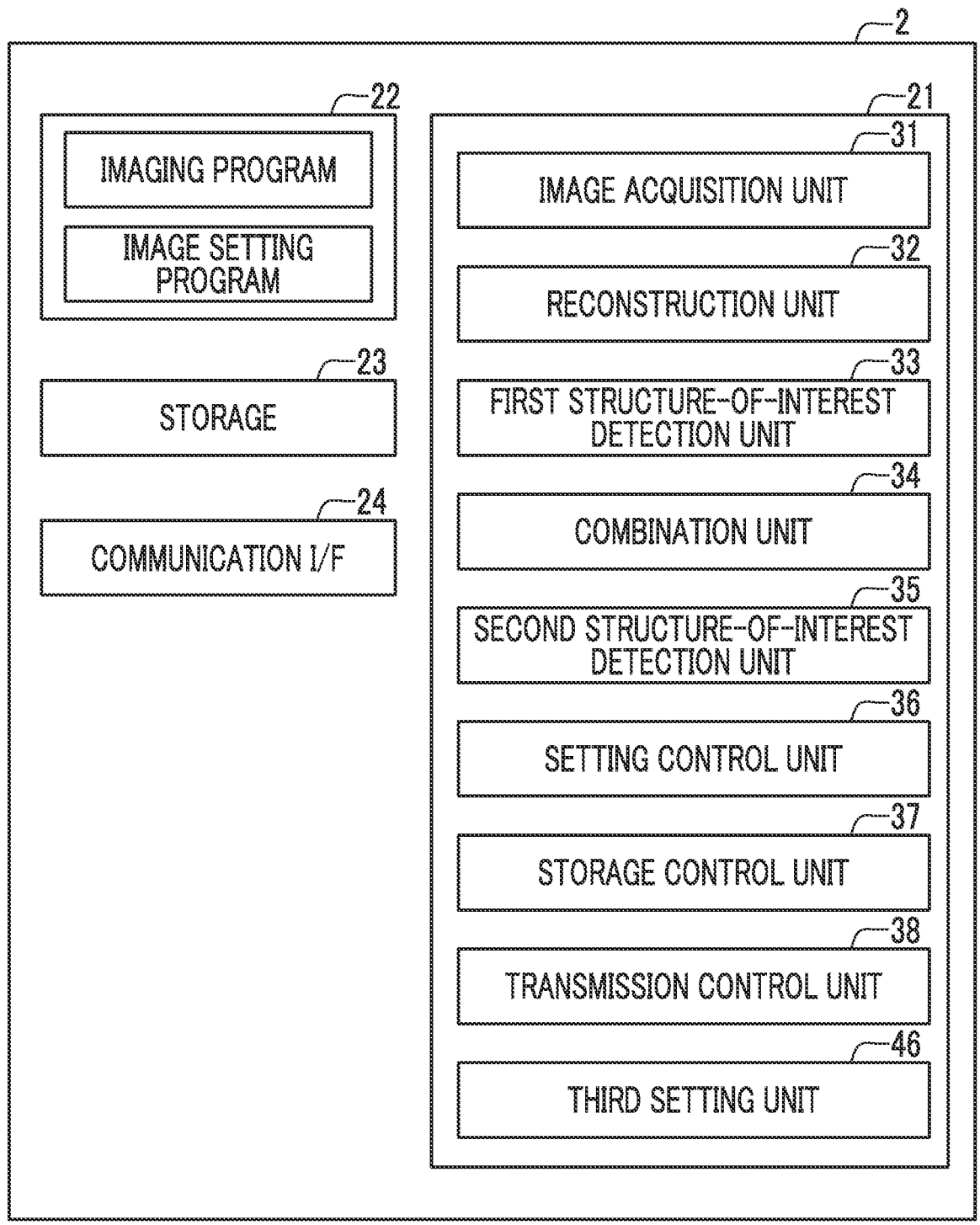
FIG. 16 is a diagram schematically illustrating a configuration of an image setting device according to a fifth embodiment that is implemented by installing the imaging program and the image setting program in the computer constituting the console.

Next, a fifth embodiment of the present disclosure will be described. FIG. 16 is a diagram schematically illustrating the configuration of an image setting device according to the fifth embodiment of the present disclosure that is implemented by installing the imaging program and the image setting program in the computer constituting the console. In addition, in FIG. 16, the same components as those in FIG. 4 are denoted by the same reference numerals, and the detailed description thereof will not be repeated. The fifth embodiment differs from the fourth embodiment in that the image setting device further comprises a third setting unit 46 that receives a setting of whether or not to determine at least some of the plurality of tomographic images Dj as the storage-required images in a case in which the second structure-of-interest detection unit 35 detects the structure of interest from the plurality of tomographic images Dj or the synthesized two-dimensional image CG1 and the setting control unit 36 sets at least some of the plurality of tomographic images Dj and the structure-highlighted synthesized two-dimensional image CG1 as the storage-required images in a case in which the structure of interest is detected from the plurality of tomographic images Dj or the synthesized two-dimensional image CG1 and the third setting unit 46 receives the setting of determining at least some of the plurality of tomographic images Dj as the storage-required images.

Figure 17:
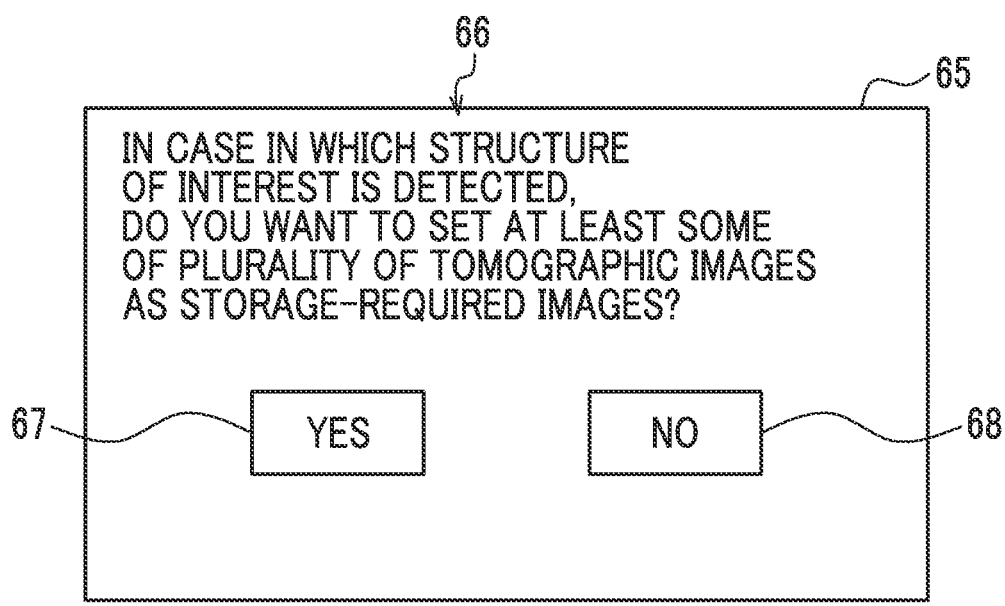
FIG. 17 is a diagram illustrating a setting screen for receiving a setting of whether or not to determine at least some of the plurality of tomographic images as the storage-required images in a case in which the structure of interest is detected.

In a case in which the second structure-of-interest detection unit 35 detects the structure of interest from the plurality of tomographic images Dj or the synthesized two-dimensional image CG1, the third setting unit 46 receives the setting of whether or not to determine at least some of the plurality of tomographic images Dj as the storage-required images. The reception of the setting of whether or not to determine at least some of the plurality of tomographic images Dj as the storage-required images may be performed by an instruction that is input from the input device 4 by the operator through a setting screen displayed on the display 3. FIG. 17 is a diagram illustrating a setting screen for receiving the setting of whether or not to determine at least some of the plurality of tomographic images Dj as the storage-required images in a case in which the structure of interest is detected. As illustrated in FIG. 17, the following are displayed on a setting screen 65: a text 66 of "In a case in which the structure of interest is detected, do you want to set at least some of the plurality of tomographic images as the storage-required images?"; a YES button 67 that is selected in a case in which the tomographic images are set as the storage-required images; and a NO button 68 that is selected in a case in which the tomographic images are not set as the storage-required images. The operator can select the YES button 67 or the NO button 68 using the input device 4 to set whether or not to determine at least some of the plurality of tomographic images Dj as the storage-required images. The result of the setting by the third setting unit 46 is stored in the storage 23.

In addition, the reception of the setting of whether or not to determine at least some of the plurality of tomographic images Dj as the storage-required images can be performed at any timing. For example, the setting can be performed before the start of imaging, before the start of the reconstruction process, before the first structure-of-interest detection process, before the structure-highlighted synthesized two-dimensional image generation process, before the second structure-of-interest detection process, or before it is determined whether or not the second structure-of-interest detection unit 35 detects the structure of interest. In this embodiment, it is assumed that the reception of the setting of whether or not to determine at least some of the plurality of tomographic images Dj as the storage-required images is performed before it is determined whether or not the second structure-of-interest detection unit 35 detects the structure of interest.

Figure 18:
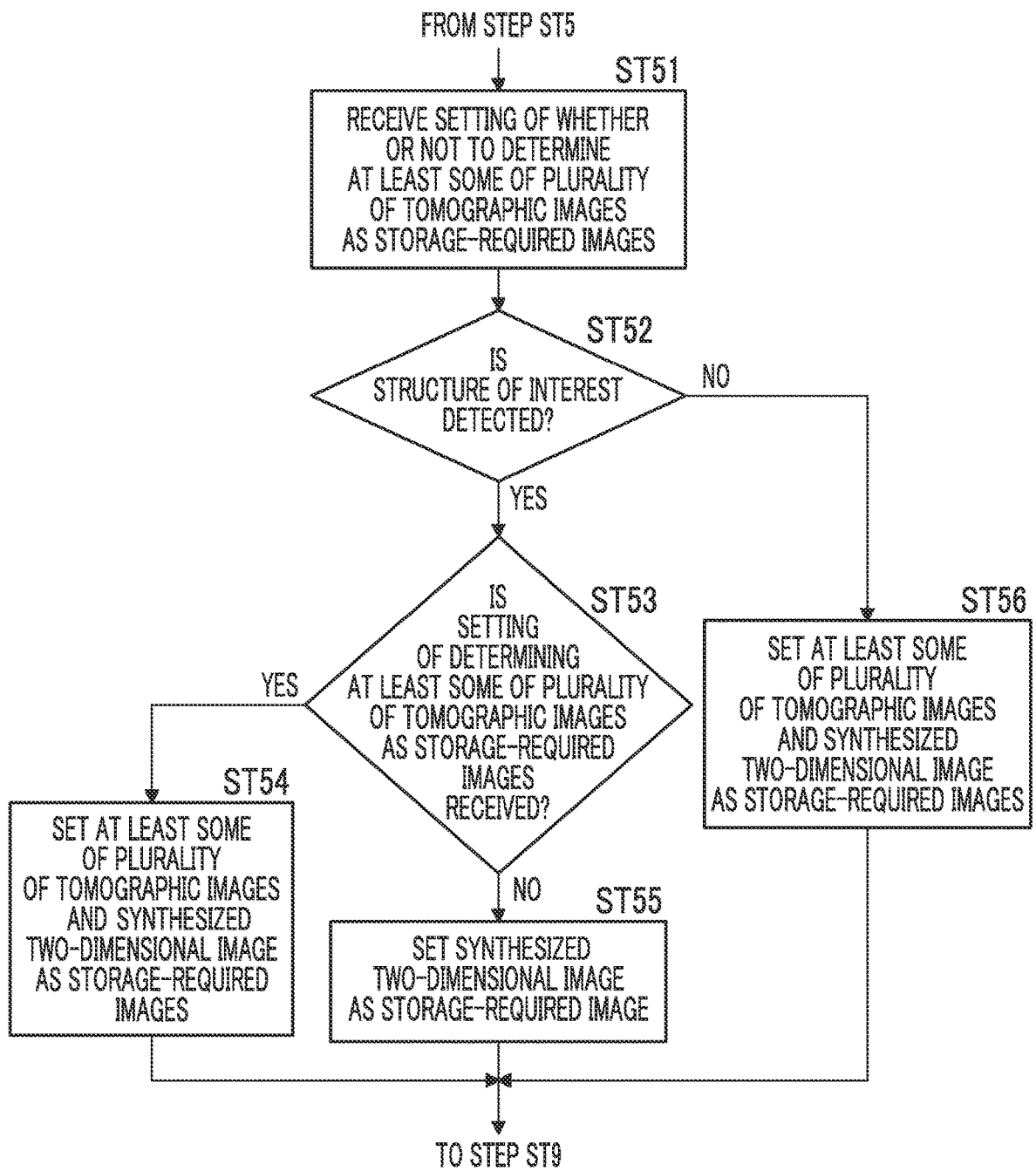
FIG. 18 is a flowchart illustrating a process performed in the fifth embodiment.

Next, a process performed in the fifth embodiment will be described. FIG. 18 is a flowchart illustrating the process performed in the fifth embodiment. In addition, in the fifth embodiment, since the processes up to the second structure-of-interest detection process are the same as the processes from Step ST1 to Step ST5 in the processes according to the first embodiment illustrated in FIG. 8, the processes after Step ST5 in FIG. 8 will be described.

In a case in which the second structure-of-interest detection unit 35 performs the process of detecting the structure of interest from the plurality of tomographic images Dj or the synthesized two-dimensional image CG1 and detects the structure of interest, the third setting unit 46 receives the setting of whether or not to determine at least some of the plurality of tomographic images Dj as the storage-required images on the basis of the instruction from the operator (Step ST51).

Then, the setting control unit 36 sets the storage-required image. That is, the setting control unit 36 determines whether or not the second structure-of-interest detection unit 35 detects the structure of interest from the plurality of tomographic images Dj or the synthesized two-dimensional image CG1 (Step ST52). In a case in which the determination result in Step ST52 is "Yes", the setting control unit 36 determines whether or not the setting of determining at least some of the plurality of tomographic images Dj as the storage-required images is received (Step ST53). In a case in which the determination result in Step ST53 is "Yes", the setting control unit 36 sets at least some of the plurality of tomographic images Dj and the synthesized two-dimensional image CG1 as the storage-required images (Step ST54). In a case in which the determination result in Step ST53 is "No", the setting control unit 36 sets at least some of the plurality of tomographic images Dj as the non-storage-required images and sets the synthesized two-dimensional image CG1 as the storage-required image (Step ST55).

In a case in which the determination result in Step ST52 is "No", that is, in a case in which the structure of interest is not detected from the plurality of tomographic images Dj or the synthesized two-dimensional image CG1, the setting control unit 36 sets at least some of the plurality of tomographic images Dj and the synthesized two-dimensional image CG1 as the storage-required images (Step ST56). In addition, since the processes after Steps ST54, ST55, and ST56 are the same as the processes after Step ST9 illustrated in FIG. 8, the detailed description thereof will not be repeated here.

Figure 19:
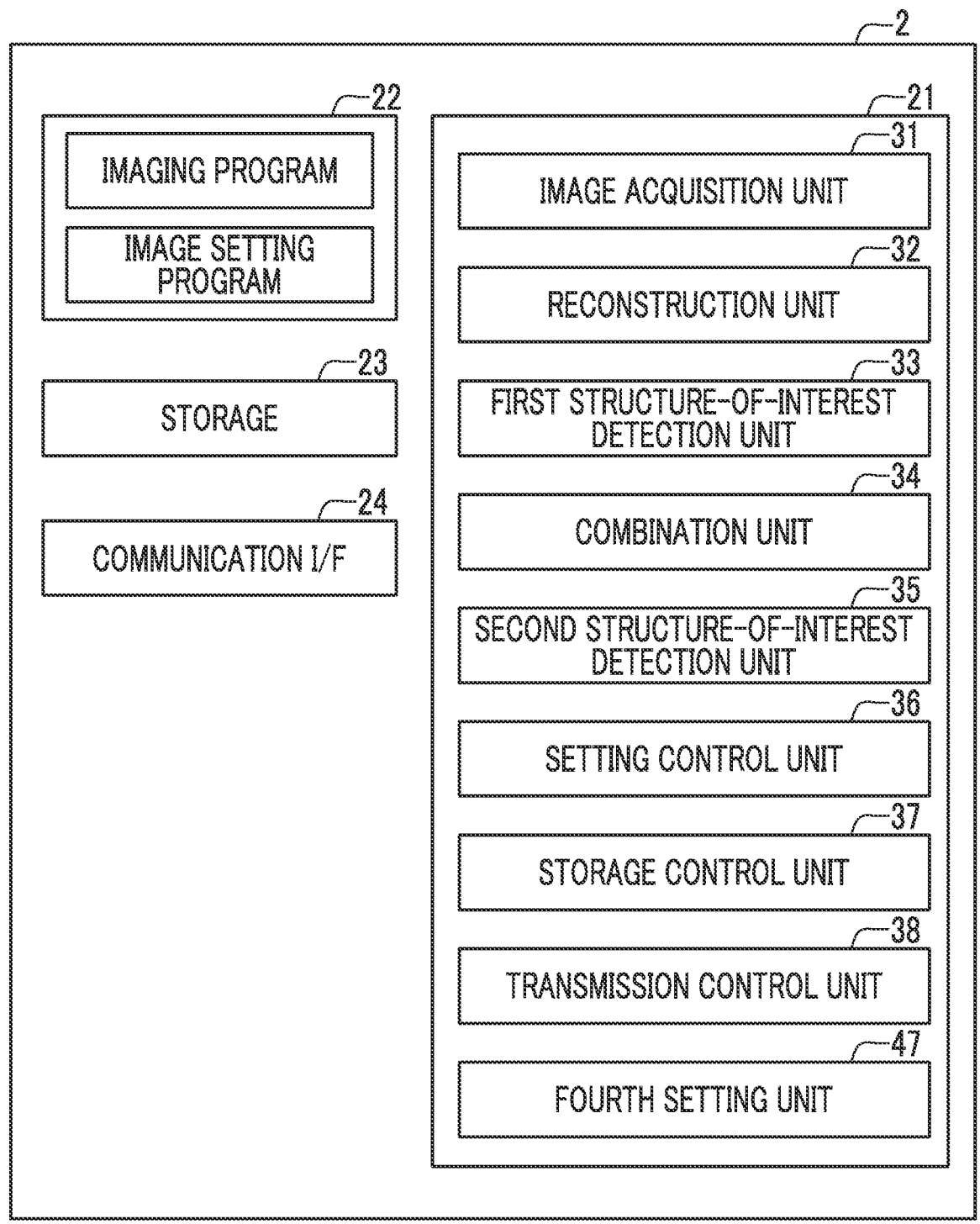
FIG. 19 is a diagram schematically illustrating a configuration of an image setting device according to a sixth embodiment that is implemented by installing the imaging program and the image setting program in the computer constituting the console.

Next, a sixth embodiment of the present disclosure will be described. FIG. 19 is a diagram schematically illustrating the configuration of an image setting device according to the sixth embodiment of the present disclosure that is implemented by installing the imaging program and the image setting program in the computer constituting the console. In addition, in FIG. 19, the same components as those in FIG. 4 are denoted by the same reference numerals, and the detailed description thereof will not be repeated. The sixth embodiment differs from the fourth embodiment in that the image setting device further comprises a fourth setting unit 47 that receives a setting of whether or not to determine at least some of the plurality of tomographic images Dj as the storage-required images in a case in which the second structure-of-interest detection unit 35 does not detect the structure of interest detected from the plurality of tomographic images Dj or the synthesized two-dimensional image CG1 and the setting control unit 36 sets at least some of the plurality of tomographic images Dj as the storage-required images only in a case in which the structure of interest is not detected from the plurality of tomographic images Dj or the synthesized two-dimensional image CG1 and the fourth setting unit 47 receives the setting of determining at least some of the plurality of tomographic images Dj as the storage-required images.

Figure 20:
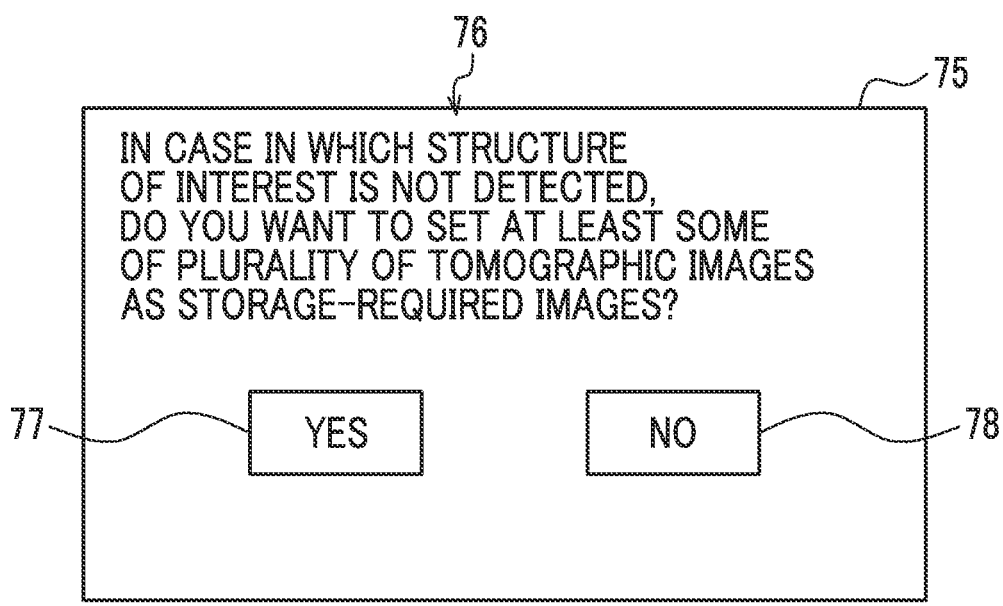
FIG. 20 is a diagram illustrating a setting screen for receiving a setting of whether or not to determine at least some of the plurality of tomographic images as the storage-required images in a case in which the structure of interest is not detected.

In a case in which the second structure-of-interest detection unit 35 does not detect the structure of interest from the plurality of tomographic images Dj or the synthesized two-dimensional image CG1, the fourth setting unit 47 receives the setting of whether or not to determine at least some of the plurality of tomographic images Dj as the storage-required images. The reception of the setting of whether or not to determine at least some of the plurality of tomographic images Dj as the storage-required images may be performed by an instruction that is input from the input device 4 by the operator through a setting screen displayed on the display 3. FIG. 20 is a diagram illustrating a setting screen for receiving the setting of whether or not to determine at least some of the plurality of tomographic images Dj as the storage-required images in a case in which the structure of interest is not detected. As illustrated in FIG. 20, the following are displayed on a setting screen 75: a text 76 of "In a case in which the structure of interest is not detected, do you want to set at least some of the plurality of tomographic images as the storage-required images?"; a YES button 77 that is selected in a case in which the tomographic images are set as the storage-required images; and a NO button 78 that is selected in a case in which the tomographic images are not set as the storage-required images. The operator can select the YES button 77 or the NO button 78 using the input device 4 to set whether or not to determine at least some of the plurality of tomographic images Dj as the storage-required images. The result of the setting by the fourth setting unit 47 is stored in the storage 23.

In addition, the reception of the setting of whether or not to determine at least some of the plurality of tomographic images Dj as the storage-required images can be performed at any timing. For example, the setting can be performed before the start of imaging, before the start of the reconstruction process, before the first structure-of-interest detection process, before the structure-highlighted synthesized two-dimensional image generation process, before the second structure-of-interest detection process, or before it is determined whether or not the second structure-of-interest detection unit 35 detects the structure of interest. In this embodiment, it is assumed that the reception of the setting of whether or not to determine at least some of the plurality of tomographic images Dj as the storage-required images is performed before it is determined whether or not the second structure-of-interest detection unit 35 detects the structure of interest.

Figure 21:
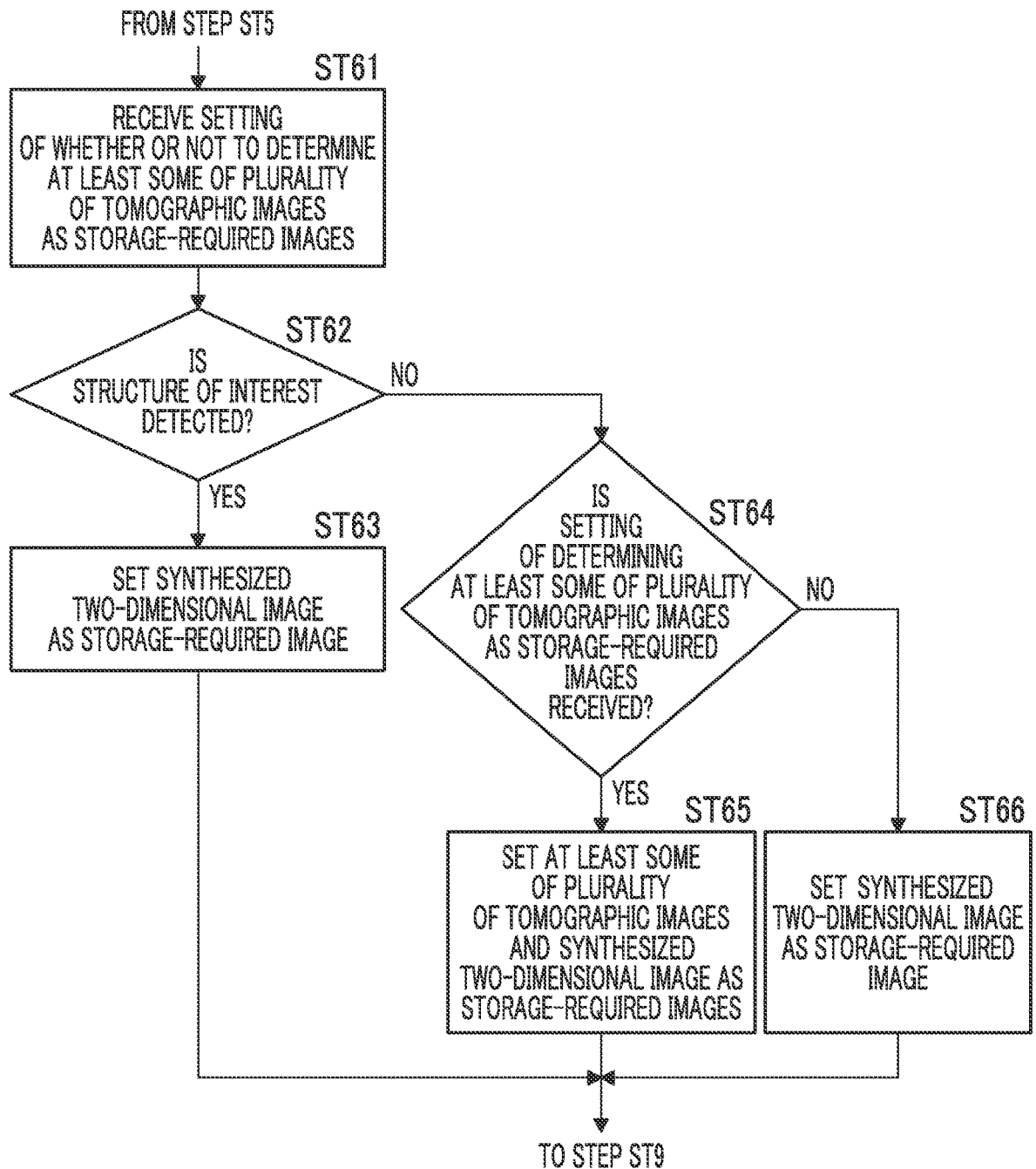
FIG. 21 is a flowchart illustrating a process performed in the sixth embodiment.

Next, a process performed in the sixth embodiment will be described. FIG. 21 is a flowchart illustrating the process performed in the sixth embodiment. In addition, in the sixth embodiment, since the processes up to the second structure-of-interest detection process are the same as the processes from Step ST1 to Step ST5 in the processes according to the first embodiment illustrated in FIG. 8, the processes after Step ST5 in FIG. 8 will be described.

In a case in which the second structure-of-interest detection unit 35 performs the process of detecting the structure of interest from the plurality of tomographic images Dj or the synthesized two-dimensional image CG1 and does not detect the structure of interest, the fourth setting unit 47 receives the setting of whether or not to determine at least some of the plurality of tomographic images Dj as the storage-required images on the basis of the instruction from the operator (Step ST61). Then, the setting control unit 36 sets the storage-required image. That is, the setting control unit 36 determines whether or not the structure of interest is detected from the plurality of tomographic images Dj or the synthesized two-dimensional image CG1 (Step ST62). In a case in which the determination result in Step ST62 is "Yes", the setting control unit 36 sets at least some of the plurality of tomographic images Dj as the non-storage-required images and sets the synthesized two-dimensional image CG1 as the storage-required image (Step ST63).

In a case in which the determination result in Step ST62 is "No", that is, in a case in which the structure of interest is not detected from the plurality of tomographic images Dj or the synthesized two-dimensional image CG1, the setting control unit 36 determines whether or not the setting of determining at least some of the plurality of tomographic images Dj as the storage-required images is received (Step ST64). In a case in which the determination result in Step ST64 is "Yes", the setting control unit 36 sets at least some of the plurality of tomographic images Dj and the synthesized two-dimensional image CG1 as the storage-required images (Step ST65). In a case in which the determination result in Step ST64 is "No", the setting control unit 36 sets at least some of the plurality of tomographic images Dj as the non-storage-required images and sets the synthesized two-dimensional image CG1 as the storage-required image (Step ST66). In addition, since the processes after Steps ST63, ST65, and ST66 are the same as the processes after Step ST9 illustrated in FIG. 8, the detailed description thereof will not be repeated here.

Further, in the sixth embodiment, the third setting unit 46 may be provided as in the fifth embodiment. In this case, in the processes after the determination result in Step ST62 is "Yes" in the flowchart illustrated in FIG. 21, the processes after Step ST53 in the flowchart illustrated in FIG. 18 are performed.

Figure 22:
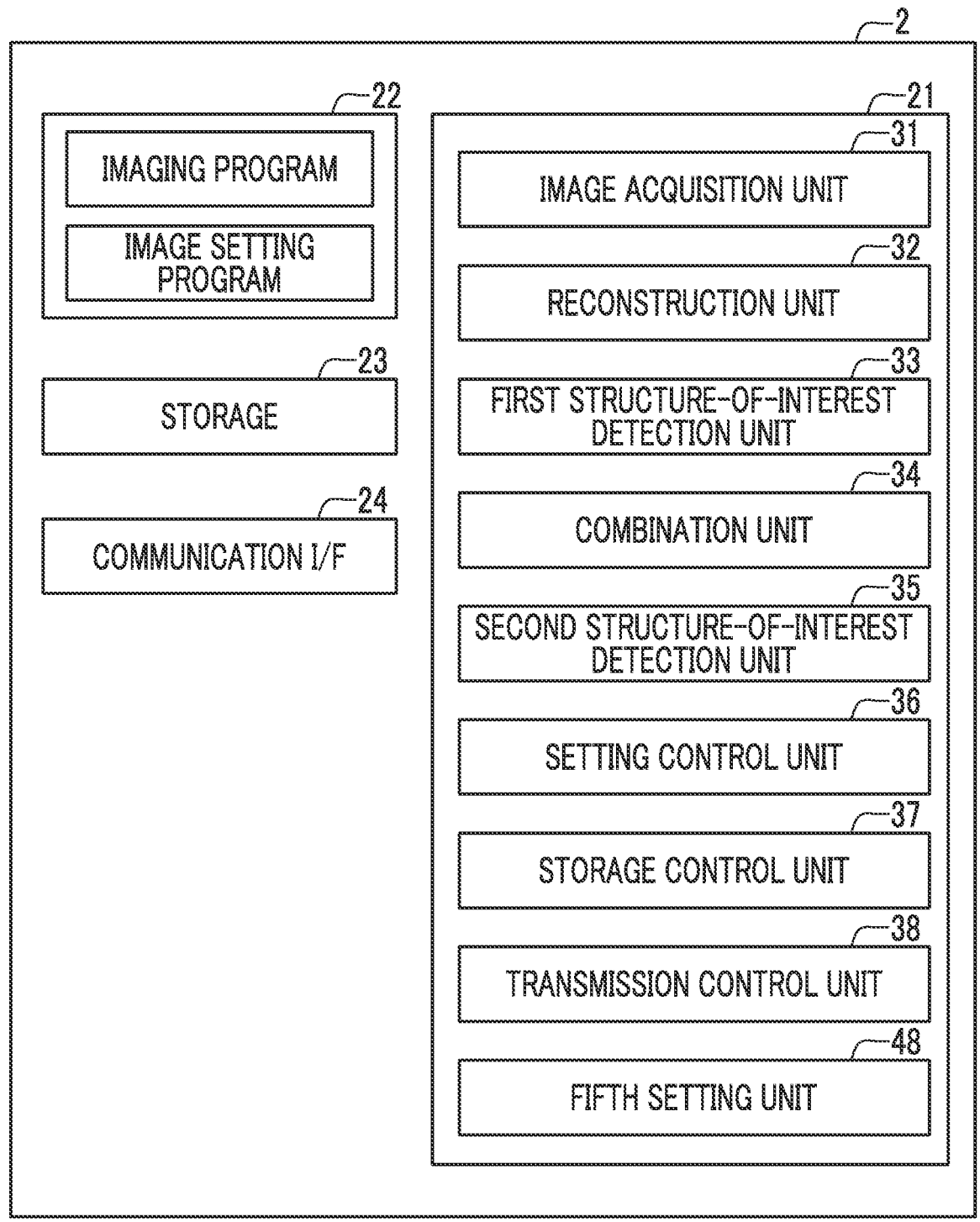
FIG. 22 is a diagram schematically illustrating a configuration of an image setting device according to a seventh embodiment that is implemented by installing the imaging program and the image setting program in the computer constituting the console.

Next, a seventh embodiment of the present disclosure will be described. FIG. 22 is a diagram schematically illustrating the configuration of an image setting device according to the seventh embodiment of the present disclosure that is implemented by installing the imaging program and the image setting program in the computer constituting the console. In addition, in FIG. 22, the same components as those in FIG. 4 are denoted by the same reference numerals, and the detailed description thereof will not be repeated. The seventh embodiment differs from the first embodiment in that the image setting device further comprises a fifth setting unit 48 that sets whether or not to generate the structure-highlighted synthesized two-dimensional image CG1 from the plurality of tomographic images Dj and the combination unit 34 generates the structure-highlighted synthesized two-dimensional image CG1 in a case in which the structure-highlighted synthesized two-dimensional image is set to be generated.

Figure 23:
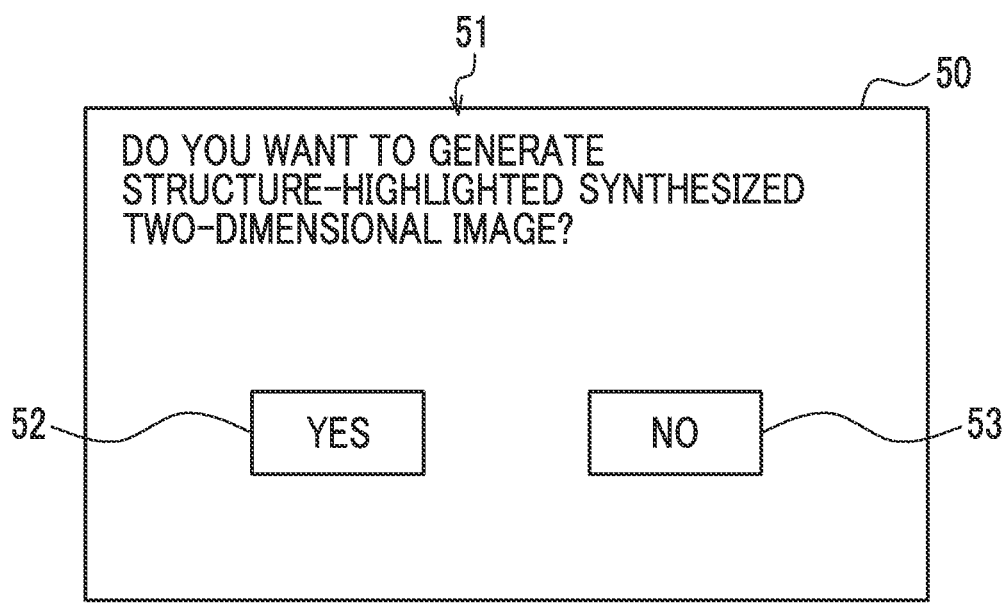
FIG. 23 is a diagram illustrating a setting screen for whether or not to generate the structure-highlighted synthesized two-dimensional image.

The fifth setting unit 48 sets whether or not to generate the structure-highlighted synthesized two-dimensional image from the plurality of tomographic images Dj. The setting of whether or not to generate the structure-highlighted synthesized two-dimensional image may be performed by an instruction that is input from the input device 4 by the operator through a setting screen displayed on the display 3. FIG. 23 is a diagram illustrating a setting screen for whether or not to generate the structure-highlighted synthesized two-dimensional image. As illustrated in FIG. 23, the following are displayed on a setting screen 50: a text 51 of "Do you want to generate a structure-highlighted synthesized two-dimensional image?"; a YES button 52 that is selected in a case in which the structure-highlighted synthesized two-dimensional image is generated; and a NO button 53 that is selected in a case in which the structure-highlighted synthesized two-dimensional image is not generated. The operator can select the YES button 52 or the NO button 53 using the input device 4 to set whether or not to generate the structure-highlighted synthesized two-dimensional image. The result of the setting by the fifth setting unit 48 is stored in the storage 23.

In addition, the setting of whether or not to generate the structure-highlighted synthesized two-dimensional image from the plurality of tomographic images Dj can be performed at any timing. For example, the setting can be performed before the start of imaging, before the start of the reconstruction process, before the first structure-of-interest detection process, or before a process of generating the structure-highlighted synthesized two-dimensional image. In this embodiment, it is assumed that the setting of whether or not to generate the structure-highlighted synthesized two-dimensional image from the plurality of tomographic images Dj is performed before the process of generating the structure-highlighted synthesized two-dimensional image.

In the seventh embodiment, in a case in which the fifth setting unit 48 sets to generate the structure-highlighted synthesized two-dimensional image, the same process as that in the first embodiment is performed. On the other hand, in a case in which the fifth setting unit 48 does not set to generate the structure-highlighted synthesized two-dimensional image, the setting control unit 36 sets at least some of the plurality of tomographic images Dj as the storage-required images. Further, in the seventh embodiment, in a case in which the structure-highlighted synthesized two-dimensional image is set not to be generated, the combination unit 34 generates another synthesized two-dimensional image that is not the structure-highlighted type. Then, the setting control unit 36 sets another synthesized two-dimensional image as the storage-required image together with at least some of the plurality of tomographic images Dj.

Here, the combination unit 34 generates another synthesized two-dimensional image CG2 as follows according to the method described in JP2014-128716A. First, the combination unit 34 performs frequency decomposition for each of the plurality of tomographic images Dj to derive a plurality of band tomographic images indicating frequency components in each of a plurality of frequency bands for each of the plurality of tomographic images Dj. Further, the combination unit 34 combines the plurality of band tomographic images for each frequency band to generate band synthesized two-dimensional images. For example, an addition method, an averaging method, a maximum intensity projection method, or a minimum intensity projection method can be used as a combination method. Then, the combination unit 34 performs weighting and frequency composition on the band synthesized two-dimensional images for each frequency band to generate another synthesized two-dimensional image CG2.

Figure 24:
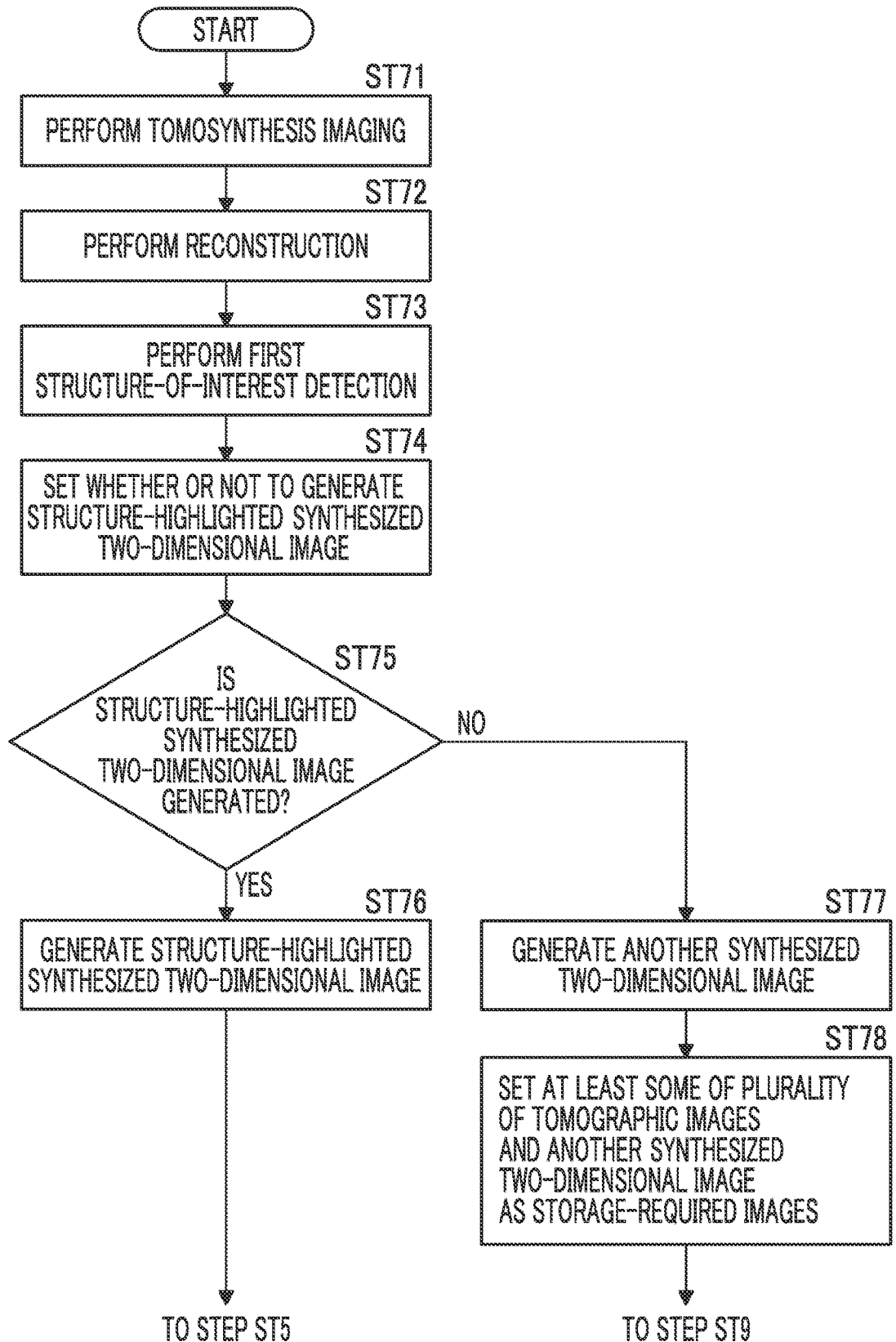
FIG. 24 is a flowchart illustrating a process performed in the seventh embodiment.

Next, a process performed in the seventh embodiment will be described. FIG. 24 is a flowchart illustrating the process performed in the seventh embodiment. First, the process is started by the input of an imaging instruction by the operator, and the image acquisition unit 31 instructs the mammography apparatus 10 to perform tomosynthesis imaging. Then, the mammography apparatus 10 performs the tomosynthesis imaging on the breast M (Step ST71). A plurality of projection images Gi are acquired by the tomosynthesis imaging. Then, the reconstruction unit 32 reconstructs the plurality of projection images Gi acquired by the tomosynthesis imaging (Step ST72). Then, a plurality of tomographic images Dj are generated. Then, the first structure-of-interest detection unit 33 detects the structure of interest from each of the plurality of tomographic images Dj (first structure-of-interest detection: Step ST73).

Then, the fifth setting unit 48 sets whether or not to generate a structure-highlighted synthesized two-dimensional image on the basis of an instruction from the operator (Step ST74). Then, the combination unit 34 generates a synthesized two-dimensional image. That is, the combination unit 34 determines whether or not the fifth setting unit 48 sets to generate a structure-highlighted synthesized two-dimensional image (Step ST75). In a case in which the determination result in Step ST75 is "Yes", the combination unit 34 generates the structure-highlighted synthesized two-dimensional image CG1 (Step ST76). In addition, since the processes after Step ST76 are the same as the processes after Step ST5 in the first embodiment illustrated in FIG. 8, the detailed description thereof will not be repeated here.

In a case in which the determination result in Step ST75 is "No", the combination unit 34 generates another synthesized two-dimensional image CG2 that is not the structure-highlighted type (Step ST77). Then, the setting control unit 36 sets at least some of the plurality of tomographic images Dj and another synthesized two-dimensional image CG2 as the storage-required images (Step ST78). In addition, since the processes after Step ST78 are the same as the processes after Step ST9 illustrated in FIG. 8, the detailed description thereof will not be repeated here.

Further, in the seventh embodiment, in a case in which the setting of generating the structure-highlighted synthesized two-dimensional image is not performed, another synthesized two-dimensional image CG2 that is not the structure-highlighted type is generated and is set as the storage-required image together with at least some of the plurality of tomographic images Dj. However, the present disclosure is not limited thereto. Only at least some of the plurality of tomographic images Dj may be set as the storage-required images without generating another synthesized two-dimensional image CG2.

Figure 25:
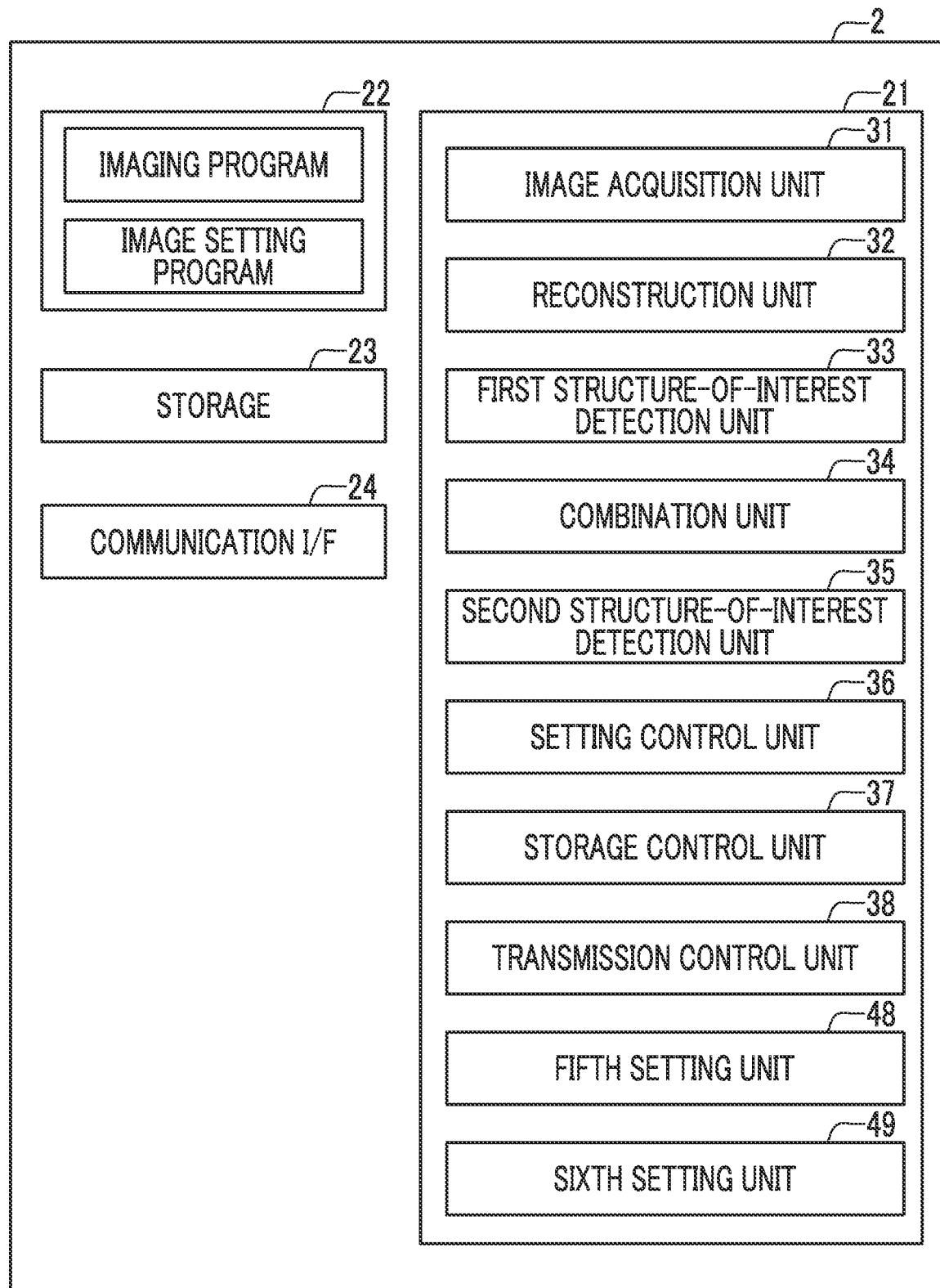
FIG. 25 is a diagram schematically illustrating a configuration of an image setting device according to an eighth embodiment that is implemented by installing the imaging program and the image setting program in the computer constituting the console.

Next, an eighth embodiment of the present disclosure will be described. FIG. 25 is a diagram schematically illustrating the configuration of an image setting device according to the eighth embodiment of the present disclosure that is implemented by installing the imaging program and the image setting program in the computer constituting the console. In addition, in FIG. 25, the same components as those in FIG. 22 are denoted by the same reference numerals, and the detailed description thereof will not be repeated. The eighth embodiment differs from the seventh embodiment in that the image setting device further comprises a sixth setting unit 49 that receives a setting of whether or not to determine at least some of the plurality of tomographic images Dj as the storage-required images in a case in which the structure-highlighted synthesized two-dimensional image is set not to be generated and the setting control unit 36 sets at least some of the plurality of tomographic images Dj as the storage-required images in a case in which the structure-highlighted synthesized two-dimensional image is set not to be generated and the setting of determining at least some of the plurality of tomographic images Dj as the storage-required images is received.

Figure 26:
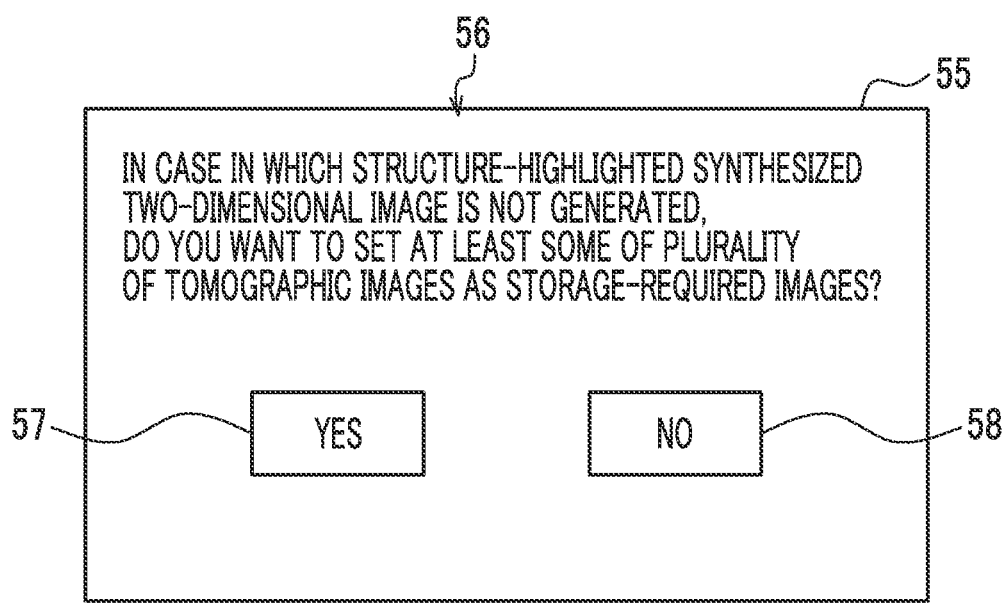
FIG. 26 is a diagram illustrating a setting screen for receiving a setting of whether or not to determine at least some of the plurality of tomographic images as the storage-required images in a case in which the structure-highlighted synthesized two-dimensional image is set not to be generated.

The sixth setting unit 49 receives the setting of whether or not to determine at least some of the plurality of tomographic images Dj as the storage-required images in a case in which the structure-highlighted synthesized two-dimensional image is set not to be generated. The reception of the setting of whether or not to determine at least some of the plurality of tomographic images Dj as the storage-required images may be performed by an instruction that is input from the input device 4 by the operator through a setting screen displayed on the display 3. FIG. 26 is a diagram illustrating a setting screen for receiving the setting of whether or not to determine at least some of the plurality of tomographic images Dj as the storage-required images in a case in which the structure-highlighted synthesized two-dimensional image is set not to be generated. As illustrated in FIG. 26, the following are displayed on a setting screen 55: a text 56 of "In a case in which the structure-highlighted synthesized two-dimensional image is not generated, do you want to set at least some of the plurality of tomographic images as the storage-required images?; a YES button 57 that is selected in a case in which the tomographic images are set as the storage-required images; and a NO button 58 that is selected in a case in which the tomographic images are not set as the storage-required images. The operator can select the YES button 57 or the NO button 58 using the input device 4 to set whether or not to set at least some of the plurality of tomographic images Dj as the storage-required images. The result of the setting by the sixth setting unit 49 is stored in the storage 23.

In addition, in a case in which the structure-highlighted synthesized two-dimensional image is set not to be generated, the reception of the setting of whether or not to determine at least some of the plurality of tomographic images Dj as the storage-required images can be performed at any timing. For example, the setting can be performed before the start of imaging, before the start of the reconstruction process, before the first structure-of-interest detection process, or before a process of generating the structure-highlighted synthesized two-dimensional image. In this embodiment, it is assumed that the reception of the setting of whether or not to determine at least some of the plurality of tomographic images Dj as the storage-required images is performed before the process of generating the structure-highlighted synthesized two-dimensional image.

Figure 27:
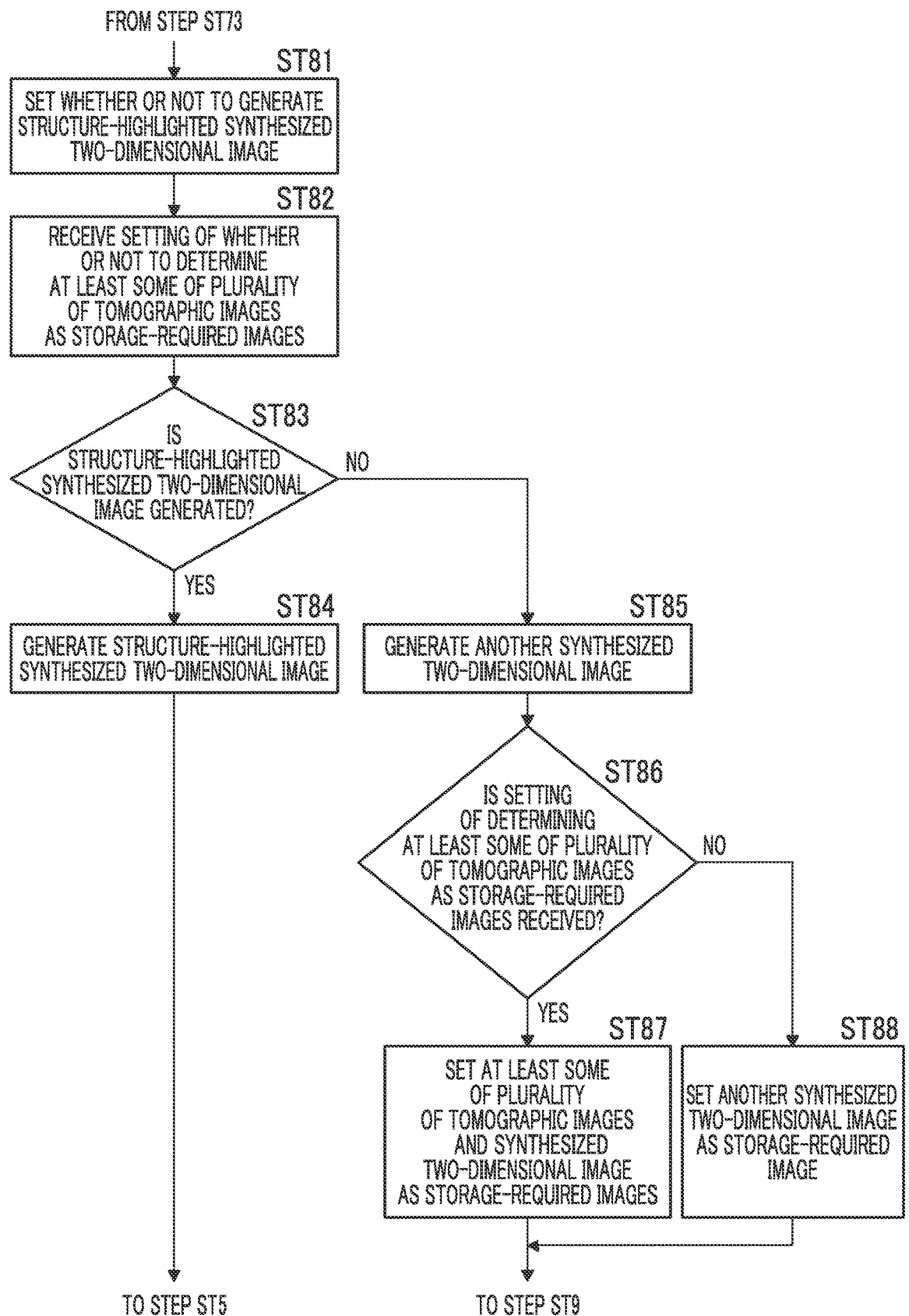
FIG. 27 is a flowchart illustrating a process performed in the eighth embodiment.

Next, a process performed in the eighth embodiment will be described. FIG. 27 is a flowchart illustrating the process performed in the tenth embodiment. In addition, in the eighth embodiment, since the processes up to the structure-of-interest detection process of the first structure-of-interest detection unit 33 are the same as the processes from Step ST71 to Step ST73 in the processes according to the seventh embodiment illustrated in FIG. 24, the processes after Step ST73 in FIG. 24 will be described here.

In a case in which the first structure-of-interest detection unit 33 detects the structure of interest from each of the plurality of tomographic images Dj, the fifth setting unit 48 sets whether or not to generate the structure-highlighted synthesized two-dimensional image, that is, the structure-highlighted synthesized two-dimensional image CG1 on the basis of the instruction from the operator (Step ST81). Then, in a case in which the structure-highlighted synthesized two-dimensional image is set not to be generated on the basis of the instruction from the operator, the sixth setting unit 49 receives the setting of whether or not to determine at least some of the plurality of tomographic images Dj as the storage-required images (Step ST82). Then, the combination unit 34 generates a synthesized two-dimensional image. That is, the combination unit 34 determines whether or not the fifth setting unit 48 is set to generate a structure-highlighted synthesized two-dimensional image (Step ST83). In a case in which the determination result in Step ST83 is "Yes", the combination unit 34 generates the structure-highlighted synthesized two-dimensional image CG1 (Step ST84). In addition, since the processes after Step ST84 are the same as the processes after Step ST5 in the first embodiment illustrated in FIG. 8, the detailed description thereof will not be repeated here.

On the other hand, in a case in which the determination result in Step ST83 is "No", the combination unit 34 generates another synthesized two-dimensional image CG2 that is not the structure-highlighted type (Step ST85). Then, the setting control unit 36 determines whether or not the setting of determining at least some of the plurality of tomographic images Dj as the storage-required images is received (Step ST86). In a case in which the determination result in Step ST86 is "Yes", the setting control unit 36 sets at least some of the plurality of tomographic images Dj and another synthesized two-dimensional image CG2 as the storage-required images (Step ST87). In a case in which the determination result in Step ST86 is "No", the setting control unit 36 sets at least some of the plurality of tomographic images Dj as the non-storage-required images and sets another synthesized two-dimensional image CG2 as the storage-required image (Step ST88). In addition, since the processes after Steps ST87 and ST88 are the same as the processes after Step ST9 illustrated in FIG. 8, the detailed description thereof will not be repeated here.

Further, in the seventh and eighth embodiments, the processes after Step ST5 in the first embodiment illustrated in FIG. 8 are performed as the processes after Step ST76 and ST84. However, the present disclosure is not limited thereto. The processes after Step ST21 in the second embodiment illustrated in FIG. 11, the processes after Step ST31 in the third embodiment illustrated in FIG. 14, the processes after Step ST41 in the fourth embodiment illustrated in FIG. 15, the processes after Step ST51 in the fifth embodiment illustrated in FIG. 18, or the processes after Step ST61 in the sixth embodiment illustrated in FIG. 21 may be performed.

Figure 28:
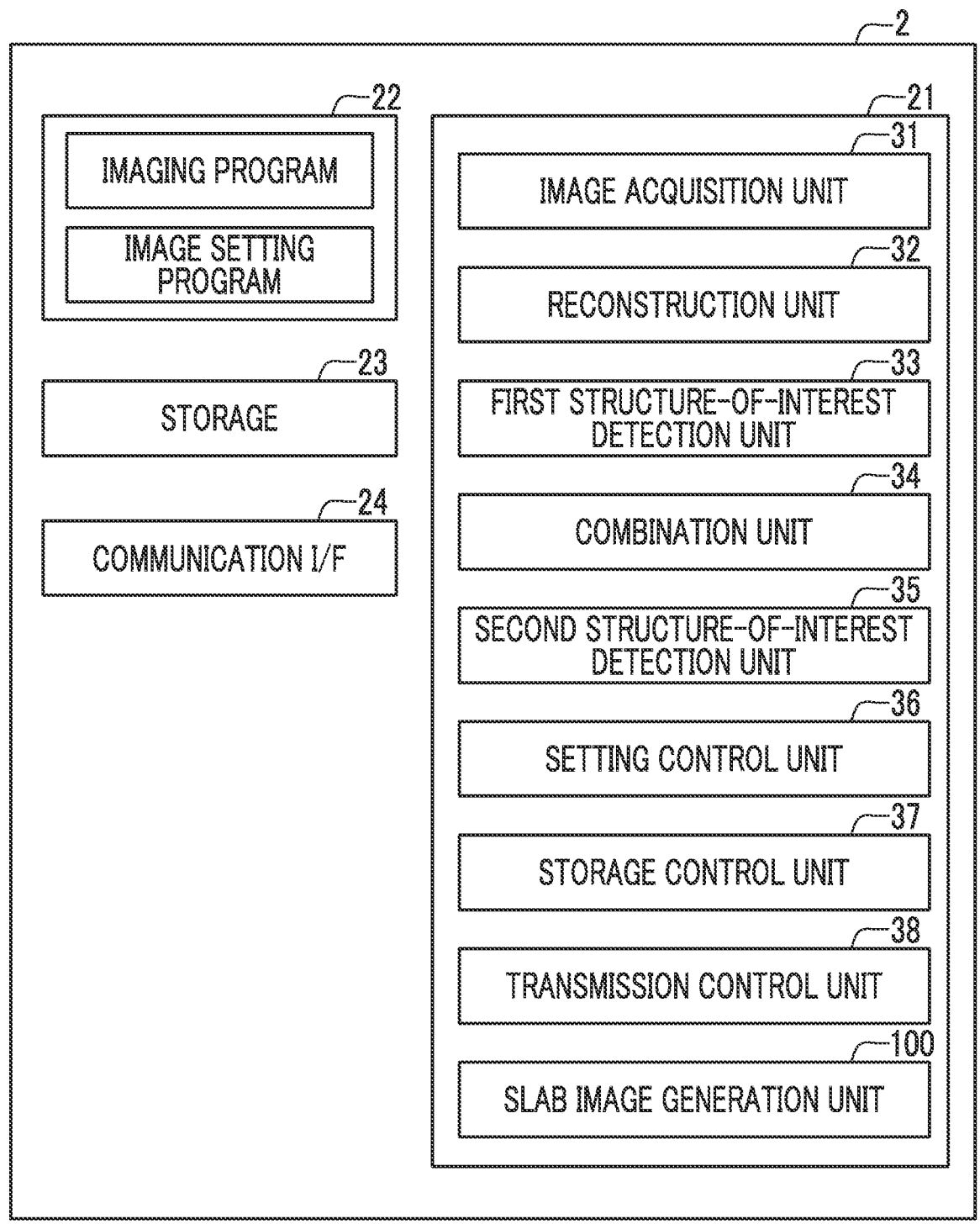
FIG. 28 is a diagram schematically illustrating a configuration of an image setting device according to a ninth embodiment that is implemented by installing the imaging program and the image setting program in the computer constituting the console.

Next, a ninth embodiment of the present disclosure will be described. FIG. 28 is a diagram schematically illustrating the configuration of an image setting device according to the ninth embodiment of the present disclosure that is implemented by installing the imaging program and the image setting program in the computer constituting the console. In addition, in FIG. 28, the same components as those in FIG. 4 are denoted by the same reference numerals, and the detailed description thereof will not be repeated. The ninth embodiment differs from the first embodiment in that the image setting device further comprises a slab image generation unit 100 which generates at least one slab image from the plurality of tomographic images Dj.

Figure 29:
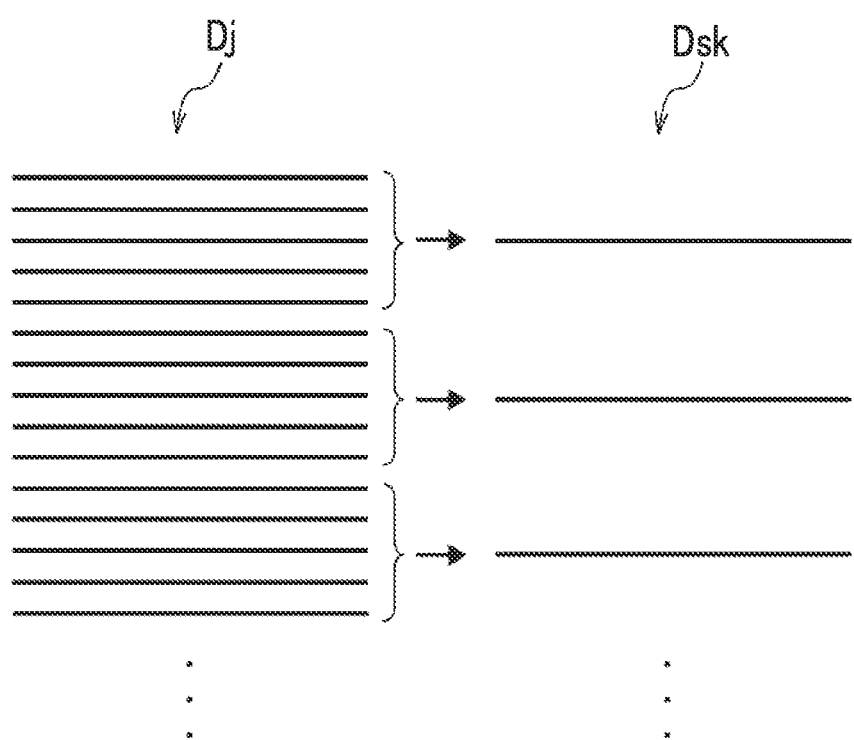
FIG. 29 is a diagram illustrating the generation of a slab image.

The slab image generation unit 100 generates at least one slab image from the plurality of tomographic images Dj. FIG. 29 is a diagram illustrating the generation of the slab image. As illustrated in FIG. 29, the slab image generation unit 100 adds a predetermined number of tomographic images (five tomographic images in FIG. 29) among the plurality of tomographic images Dj to generate one slab image Dsk. Then, one slab image Dsk is generated for every five tomographic images among the plurality of tomographic images Dj.

In the ninth embodiment, the generated slab images Dsk are set as the storage-required images as at least some of the plurality of tomographic images Dj. Therefore, in a case in which the plurality of tomographic images Dj are set as the storage-required images, the slab images Dsk are set as the storage-required images as at least some of the plurality of tomographic images Dj and are then stored or transmitted. Therefore, the amount of data can be less than that in a case in which the plurality of tomographic images Dj are stored or transmitted. As a result, it is possible to reduce the cost of storage or transmission.

In the ninth embodiment, the slab image generation unit 100 is provided in the image setting device according to the first embodiment. However, the present disclosure is not limited thereto. The slab image generation unit 100 may be provided in the image setting device according to the second to eighth embodiments.

Further, in each of the above-described embodiments, the image set as the storage-required image is stored in the storage 23 and transmitted to the PACS 7. However, the present disclosure is not limited thereto. Only the storage of the image set as the storage-required image in the storage 23 or only the transmission of the image to the PACS 7 may be performed.

Figure 30:
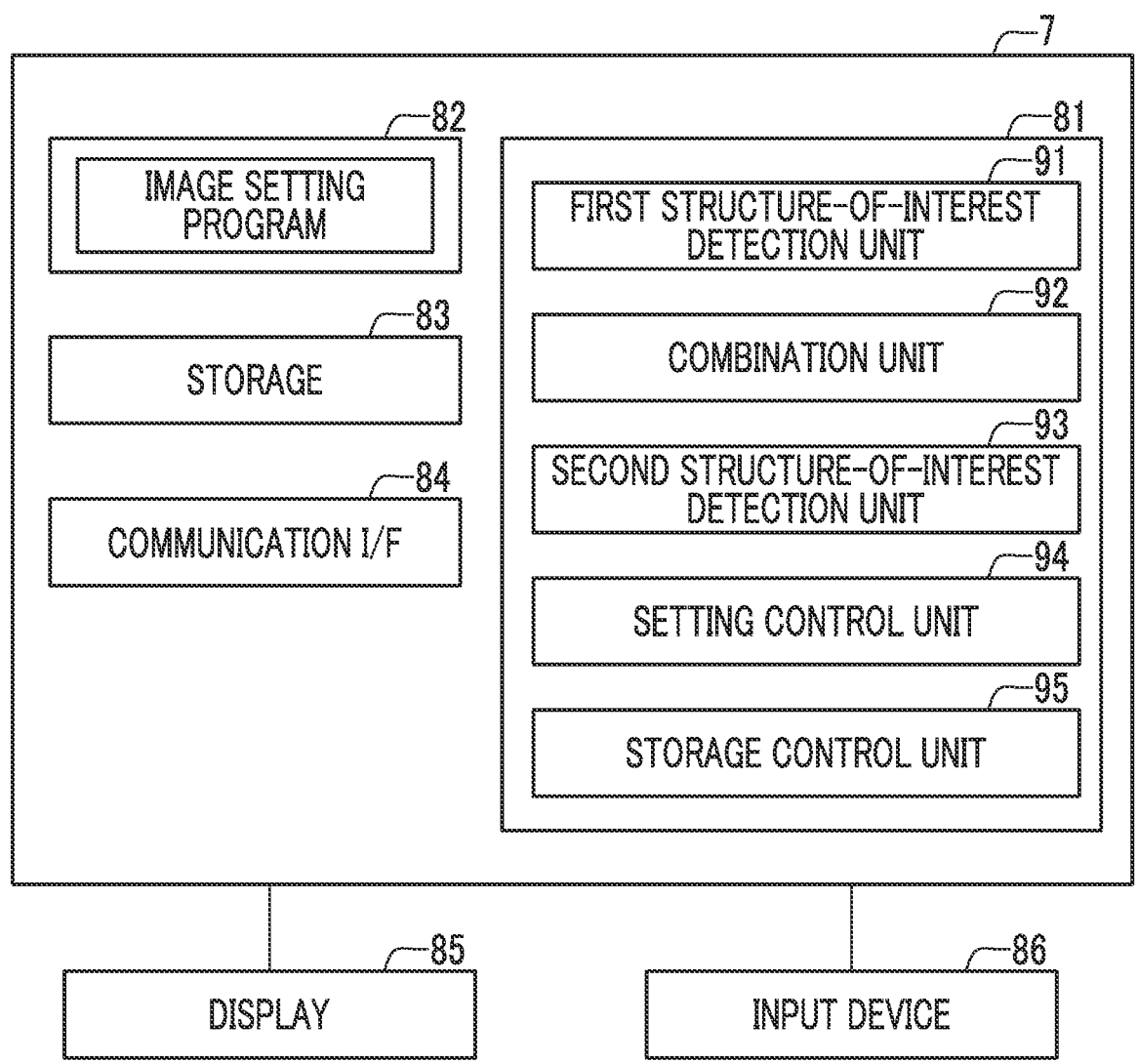
FIG. 30 is a diagram schematically illustrating a configuration of an image setting device according to a tenth embodiment that is implemented by installing the imaging program and the image setting program in a computer constituting a PACS.

In each of the above-described embodiments, the console 2 performs the image setting process. However, the present disclosure is not limited thereto. All of the plurality of tomographic images Dj generated in the console 2 may be transmitted to the PACS 7, and the PACS 7 may perform, for example, the first structure-of-interest detection process, the combination process, the second structure-of-interest detection process, and the setting control process. FIG. 30 is a diagram schematically illustrating the configuration of an image setting device according to a tenth embodiment that is implemented by installing the imaging program and the image setting program in the computer constituting the PACS 7. Further, in the tenth embodiment, it is assumed that the PACS 7 performs the same processes as those in the first embodiment.

As illustrated in FIG. 30, the PACS 7 comprises a CPU 81, a memory 82, a storage 83, a communication I/F 84, a display 85, and an input device 86 as a standard computer configuration. Since the CPU 81, the memory 82, the storage 83, the communication I/F 84, the display 85, and the input device 86 have the same functions as the CPU 21, the memory 22, the storage 23, the communication I/F 24, the display 3, and the input device 4 in the first embodiment, the detailed description thereof will not be repeated here.

In the tenth embodiment, the CPU 81 executes the image setting process according to the image setting program according to the tenth embodiment to function as a first structure-of-interest detection unit 91, a combination unit 92, a second structure-of-interest detection unit 93, a setting control unit 94, and a storage control unit 95.

Figure 31:
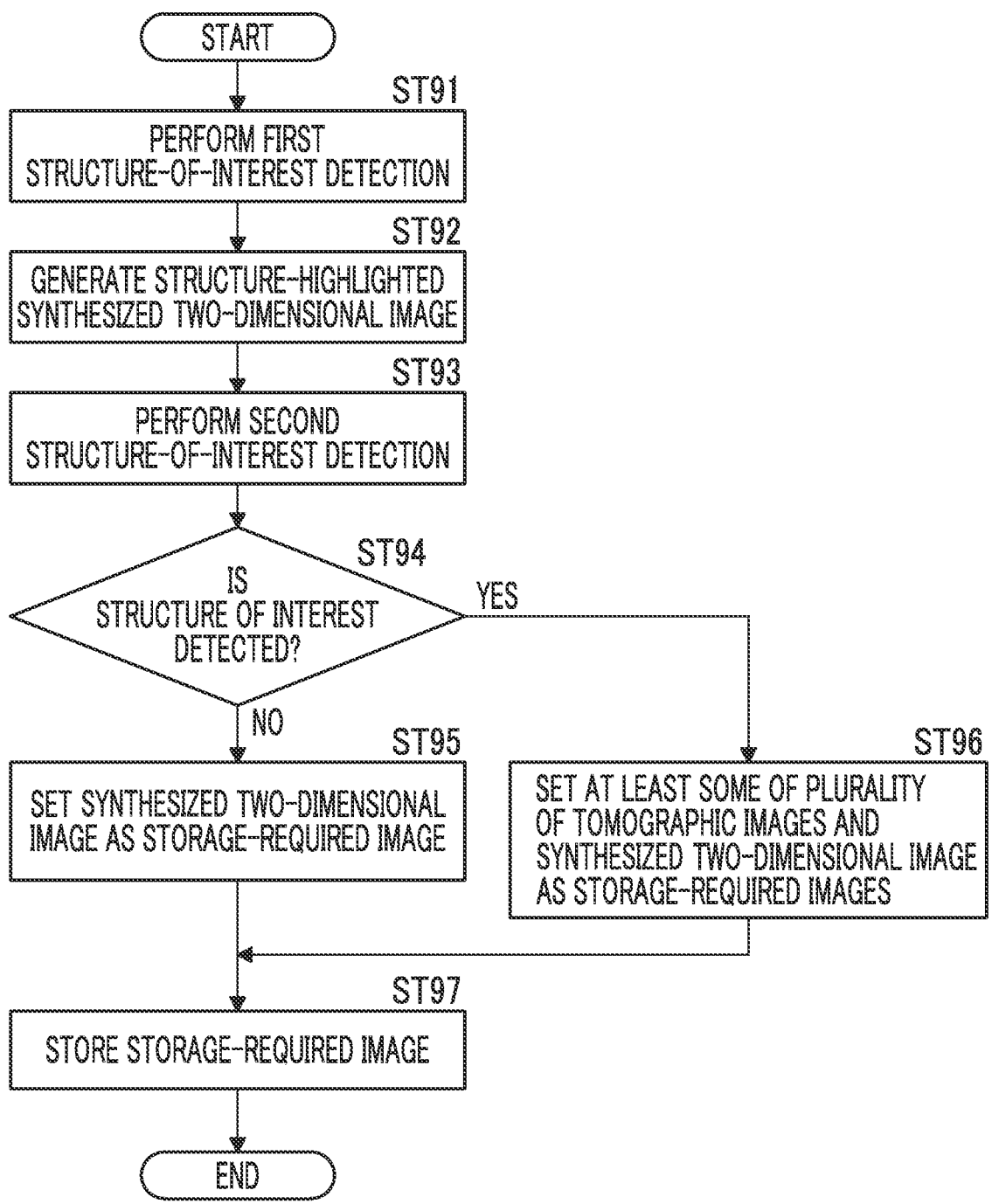
FIG. 31 is a flowchart illustrating a process performed in the tenth embodiment.

Next, a process performed in the tenth embodiment will be described. FIG. 31 is a flowchart illustrating the process performed in the tenth embodiment. In addition, in the tenth embodiment, it is assumed that the plurality of tomographic images Dj are transmitted from the radiography system 1 to the PACS 7 and are then stored in the storage 83. The process is started in response to a process start instruction from the operator of the PACS 7, and the first structure-of-interest detection unit 91 detects the structure of interest from each of the plurality of tomographic images Dj (first structure-of-interest detection: Step ST91).

Then, the combination unit 92 generates the structure-highlighted synthesized two-dimensional image CG1 using the structure of interest detected by the first structure-of-interest detection unit 91 (Step ST92). Then, the second structure-of-interest detection unit 93 detects the structure of interest from the plurality of tomographic images Dj or the synthesized two-dimensional image CG1 (second structure-of-interest detection: Step ST93).

Then, the setting control unit 94 sets the storage-required image. That is, the setting control unit 94 determines whether or not the second structure-of-interest detection unit 93 detects the structure of interest from the plurality of tomographic images Dj or the synthesized two-dimensional image CG1 (Step ST94). In a case in which the determination result in Step ST94 is "No", the setting control unit 94 sets at least some of the plurality of tomographic images Dj as the non-storage-required images and sets the synthesized two-dimensional image CG1 as the storage-required image (Step ST95). On the other hand, in a case in which the determination result in Step ST94 is "Yes", the setting control unit 94 sets at least some of the plurality of tomographic images Dj and the synthesized two-dimensional image CG1 as the storage-required images (Step ST96).

Then, the storage control unit 95 stores the images set as the storage-required images in the storage 23 (Step ST97). Then, the process ends. In this case, the plurality of tomographic images Dj stored in the storage 83 are deleted as needed.

In the tenth embodiment, the PACS 7 may receive the transmission of the projection images from the radiography system 1 instead of the plurality of tomographic images Dj. In this case, the PACS 7 is provided with a reconstruction unit, and the reconstruction unit generates a tomographic image from a plurality of projection images and uses the tomographic image for the process.

Further, in the tenth embodiment, the PACS 7 performs the processes according to the first embodiment. However, the present disclosure is not limited thereto. Of course, the PACS 7 may perform any of the processes according to the second to ninth embodiments.

Further, in each of the above-described embodiments, the first structure-of-interest detection unit 33 or 91 and the second structure-of-interest detection unit 35 or 93 detect the structure of interest from the plurality of tomographic images Dj using the CAD. However, the present disclosure is not limited thereto. The plurality of tomographic images Dj may be displayed on the display 3 such that the operator observes the tomographic images Dj to designate the structure of interest in the tomographic images Dj.

Further, in each of the above-described embodiments, the setting control unit 36 sets at least some of the plurality of tomographic images Dj as the non-storage-required images or the storage-required images according to the detection result of the structure of interest from the plurality of tomographic images Dj or the synthesized two-dimensional image CG1 by the second structure-of-interest detection unit 35. However, the present disclosure is not limited thereto. At least of some of the plurality of tomographic images Dj may be set as the non-storage-required images or the storage-required images according to the detection result of the structure of interest from at least some of the plurality of tomographic images Dj in a case in which the first structure-of-interest detection unit 33 generates the structure-highlighted synthesized two-dimensional image CG1. In this case, in each of the above-described embodiments, the second structure-of-interest detection unit 35 is not necessary.

Further, the radiation in each of the above-described embodiments is not particularly limited. For example, α-rays or γ-rays can be applied in addition to the X-rays.

Further, in each of the above-described embodiments, for example, the following various processors can be used as the hardware structures of the processing units executing various processes, such as the image acquisition unit 31, the reconstruction unit 32, the first structure-of-interest detection unit 33, the combination unit 34, the second structure-of-interest detection unit 35, the setting control unit 36, the storage control unit 37, the transmission control unit 38, the first setting unit 39, the second setting unit 45, the third setting unit 46, the fourth setting unit 47, the fifth setting unit 48, the sixth setting unit 49, and the slab image generation unit 100 of the console 2 which is the image setting device, and the first structure-of-interest detection unit 91, the combination unit 92, the second structure-of-interest detection unit 93, the setting control unit 94, and the storage control unit 95 of the PACS 7 which is the image setting device. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image setting device comprising:
   at least one processor,
   wherein the processor is configured to:
   generate a structure-highlighted synthesized two-dimensional image from a plurality of tomographic images,
   detect a structure of interest from the plurality of tomographic images or the structure-highlighted synthesized two-dimensional image, and
   set at least some of the plurality of tomographic images as either storage-required images or non-storage-required images based on a detection result of the structure of interest,
   receive a setting of determining at least some of the plurality of tomographic images as the storage-required images or the non-storage-required images in a case in which the structure of interest is detected, and
   set at least some of the plurality of tomographic images as the non-storage-required images and set the structure-highlighted synthesized two-dimensional image as a storage-required image in a case in which the structure of interest is detected and the setting of determining at least some of the plurality of tomographic images as the non-storage-required images is received.

2. The image setting device according to claim 1, wherein the processor is configured to set at least some of the plurality of tomographic images and the structure-highlighted synthesized two-dimensional image as the storage-required images in a case in which the structure of interest is detected.

3. The image setting device according to claim 1, wherein the processor is configured to set at least some of the plurality of tomographic images as the non-storage-required images and to set the structure-highlighted synthesized two-dimensional image as a storage-required image in a case in which the structure of interest is not detected.

4. The image setting device according to claim 1, wherein the processor is configured to set at least some of the plurality of tomographic images as the non-storage-required images and to set the structure-highlighted synthesized two-dimensional image as a storage-required image in a case in which the structure of interest is detected.

5. The image setting device according to claim 1, wherein the processor is configured to set at least some of the plurality of tomographic images and the structure-highlighted synthesized two-dimensional image as the storage-required images in a case in which the structure of interest is not detected.

6. The image setting device according to claim 1, wherein the processor is configured to
receive a setting of determining at least some of the plurality of tomographic images as the storage-required images or the non-storage-required images in a case in which the structure of interest is not detected, and
set at least some of the plurality of tomographic images and the structure-highlighted synthesized two-dimensional image as the storage-required images in a case in which the structure of interest is not detected and the setting of determining at least some of the plurality of tomographic images as the storage-required images is received.

7. The image setting device according to claim 6, wherein the processor is configured to set at least some of the plurality of tomographic images as the non-storage-required images and to set the structure-highlighted synthesized two-dimensional image as a storage-required image in a case in which the structure of interest is detected.

8. The image setting device according to claim 6, wherein the processor is configured to set at least some of the plurality of tomographic images and the structure-highlighted synthesized two-dimensional image as the storage-required images in a case in which the structure of interest is detected.

9. The image setting device according to claim 1, wherein the processor is configured to
receive a setting of determining at least some of the plurality of tomographic images as the storage-required images or the non-storage-required images in a case in which the structure of interest is not detected, and
set at least some of the plurality of tomographic images as the non-storage-required images and set the structure-highlighted synthesized two-dimensional image as a storage-required image in a case in which the structure of interest is not detected and the setting of determining at least some of the plurality of tomographic images as the non-storage-required images is received.

10. The image setting device according to claim 1, wherein the processor is configured to
receive a setting of determining at least some of the plurality of tomographic images as the storage-required images or the non-storage-required images in a case in which the structure of interest is detected, and
set at least some of the plurality of tomographic images and the structure-highlighted synthesized two-dimensional image as the storage-required images in a case in which the structure of interest is detected and the setting of determining at least some of the plurality of tomographic images as the storage-required images is received.

11. The image setting device according to claim 10, wherein the processor is configured to set at least some of the plurality of tomographic images as the non-storage-required images and to set the structure-highlighted synthesized two-dimensional image as a storage-required image in a case in which the structure of interest is not detected.

12. The image setting device according to claim 10, wherein the processor is configured to set at least some of the plurality of tomographic images and the structure-highlighted synthesized two-dimensional image as the storage-required images in a case in which the structure of interest is not detected.

13. The image setting device according to claim 1, wherein the processor is configured to store an image set as a storage-required image in a storage.

14. The image setting device according to claim 13, wherein the processor is configured to store information indicating a detection result of the structure of interest in the storage.

15. The image setting device according to claim 1, wherein the processor is configured to transmit an image set as a storage-required image to an external device.

16. The image setting device according to claim 15, wherein the processor is configured to transmit information indicating a detection result of the structure of interest to the external device.

17. The image setting device according to claim 1, wherein at least some of the plurality of tomographic images are tomographic images in which the structure of interest has been detected.

18. The image setting device according to claim 1, wherein at least some of the plurality of tomographic images are a plurality of slab images obtained by increasing a thickness of each of the plurality of tomographic images.

19. The image setting device according to claim 1, wherein the processor is further configured to reconstruct a plurality of projection images acquired by performing tomosynthesis imaging on an object to acquire the plurality of tomographic images.

20. The image setting device according to claim 1, wherein an object included in the plurality of tomographic images is a breast, and
the structure of interest includes at least one candidate of a calcification, a tumor, or a spicula.

21. An image setting device, comprising:
at least one processor,
wherein the processor is configured to:
generate a structure-highlighted synthesized two-dimensional image from a plurality of tomographic images,
detect a structure of interest from the plurality of tomographic images or the structure-highlighted synthesized two-dimensional image, and
set at least some of the plurality of tomographic images as either storage-required images or non-storage-required images based on a detection result of the structure of interest,
wherein the processor is configured to set whether or not to generate the structure-highlighted synthesized two-dimensional image from the plurality of tomographic images and to generate the structure-highlighted synthesized two-dimensional image in a case in which the structure-highlighted synthesized two-dimensional image is set to be generated.

22. The image setting device according to claim 21, wherein the processor is configured to set at least some of the plurality of tomographic images as the storage-required images in a case in which the structure-highlighted synthesized two-dimensional image is set not to be generated.

23. The image setting device according to claim 21, wherein the processor is configured to
receive a setting of determining at least some of the plurality of tomographic images as the storage-required images or the non-storage-required images in a case in which the structure-highlighted synthesized two-dimensional image is set not to be generated, and
set at least some of the plurality of tomographic images as the storage-required images in a case in which the setting of determining at least some of the plurality of tomographic images as the storage-required images is received.

24. The image setting device according to claim 21, wherein, in a case in which the structure-highlighted synthesized two-dimensional image is set not to be generated, the processor is configured to generate another synthesized two-dimensional image different from the structure-highlighted synthesized two-dimensional image from the plurality of tomographic images and to set another synthesized two-dimensional image as a storage-required image.

25. An image setting method comprising:
setting whether or not to generate a structure-highlighted synthesized two-dimensional image from a plurality of tomographic images of an object;
in a case in which the structure-highlighted synthesized two-dimensional image is set to be generated, generating the structure-highlighted synthesized two-dimensional image from the plurality of tomographic images of the object;
detecting a structure of interest from the plurality of tomographic images or the structure-highlighted synthesized two-dimensional image; and
setting at least some of the plurality of tomographic images as either storage-required images or non-storage-required images based on a detection result of the structure of interest.

26. A non-transitory computer-readable storage medium that stores an image setting program that causes a computer to execute:
a procedure of setting whether or not to generate a structure-highlighted synthesized two-dimensional image from a plurality of tomographic images of an object;
a procedure of, in a case in which the structure-highlighted synthesized two-dimensional image is set to be generated, generating the structure-highlighted synthesized two-dimensional image from the plurality of tomographic images of the object;
a procedure of detecting a structure of interest from the plurality of tomographic images and the structure-highlighted synthesized two-dimensional image; and
a procedure of setting at least some of the plurality of tomographic images as either storage-required images or non-storage-required images based on a detection result of the structure of interest.

\* \* \* \* \*